US008435496B2

(12) United States Patent
Brougham et al.

(10) Patent No.: US 8,435,496 B2
(45) Date of Patent: May 7, 2013

(54) NANOPARTICLE CLUSTERS AND METHODS FOR FORMING SAME

(75) Inventors: Dermot Brougham, Dublin (IE); Swapankumar Ghosh, Trivandrum (IN)

(73) Assignee: Dublin City University, Dublin (IE)

(*) Notice: Subject to any disclaimer, the term of this patent is extended or adjusted under 35 U.S.C. 154(b) by 677 days.

(21) Appl. No.: 12/519,132

(22) PCT Filed: Dec. 12, 2007

(86) PCT No.: PCT/EP2007/063815
§ 371 (c)(1),
(2), (4) Date: Dec. 21, 2009

(87) PCT Pub. No.: WO2008/071742
PCT Pub. Date: Jun. 19, 2008

(65) Prior Publication Data
US 2010/0104514 A1    Apr. 29, 2010

(30) Foreign Application Priority Data
Dec. 12, 2006  (EP) ..................................... 06125979

(51) Int. Cl.
*A61K 9/14* (2006.01)
*A61K 47/02* (2006.01)
*A61K 49/18* (2006.01)
*C01G 7/00* (2006.01)
*C01G 49/00* (2006.01)
*C01G 49/02* (2006.01)
*C01G 49/08* (2006.01)

(52) U.S. Cl.
USPC ................. 424/9.3; 252/62.51 R; 252/62.55; 252/62.56; 424/489; 424/617; 424/646; 424/649; 514/769; 977/773; 977/904

(58) Field of Classification Search .......................... None
See application file for complete search history.

(56) References Cited

U.S. PATENT DOCUMENTS
2005/0175702 A1* 8/2005 Muller-Schulte ............. 424/486

FOREIGN PATENT DOCUMENTS
WO   2005/076938 A3   8/2005

OTHER PUBLICATIONS

S Sun, H Zeng. "Size-Controlled Synthesis of Magnetite Nanoparticles." Journal of the American Chemical Society, vol. 124, 2002, pp. 8204-8205.*

NR Jana, L Gearheart, CJ Murphy. "Evidence for Seed-Mediated Nucleation in the Chemical Reduction of Gold Salts to Gold Nanoparticles." Chem. Mater., vol. 13, 2001, pp. 2313-2322.*
A Martino, SA Yamanaka, JS Kawola, DA Loy. "Encapsulation of Gold Nanoclusters in Silica Materials via an Inverse Micelle/Sol-Gel Synthesis." Chem. Mater., vol. 9, 1997, pp. 423-429.*
JF Berret, N Schonbeck, F Gazeau, D El Kharrat, O Sandre, A Vacher, M Airiau. "Controlled Clustering of Superparamagnetic Nanoparticles Using Block Copolymers: Design of New Contrast Agents for Magnetic Resonance Imaging." Journal of the American Chemical Society, vol. 128, 2006, pp. 1755-1761, Available Online Jan. 13, 2006.*
J Xie, S Peng, N Brower, N Pourmand, SX Wang, S Sun. "One-pot synthesis of monodisperse iron oxide nanoparticles for potential biomedical applications." Pure and Applied Chemistry, vol. 78 No. 5, 2006, pp. 1003-1014. First Published Aug. 14-19, 2005.*
Definition "Single Crystal," Wikipedia, the free encyclopedia, URL=http://en.wikipedia.org/wiki/Single_crystal, last updated May 2, 2012, downloaded May 12, 2012, 4 Pages.
Henglein, et al., "Formation of Colloidal Silver Nanoparticles: Capping Action of Citrate," J. Phys. Chem. B. 103 (44):9533-9539, 1999.
Lee et al., "A Comparison of Coprecipitation with Microemulsion Methods in the Preparation of Magnetite," Journal of Applied Physics 85(8):5231-5233, 1999.
Shen et al., "Polymerization of Olefin-Terminated Surfactant Bilayers on Magnetic Fluid Nanoparticles," Langmuir 16 (25):9907-9911, 2000.
Sun et al., "Size-Controlled Synthesis of Magnetite Nanoparticles," J. Am. Chem. Soc. 124(28):8204-8205, 2002.
Jana et al., "Size- and Shape-Controlled Magnetic (Cr, Mn, Fe, Co, Ni) Oxide Nanocrystals via a Simple and General Approach," Chem. Mater. 16(20):3931-3935, 2004.
Ditsch et al., "Controlled Clustering and Enhanced Stability of Polymer-Coated Magnetic Nanoparticles," Langmuir 21 (13):6006-6018, 2005.
Huh et al., "In Vivo Magnetic Resonance Detection of Cancer by Using Multifunctional Magnetic Nanocrystals," J. Am. Chem. Soc. 127(35):12387-12391, 2005.
Jun et al., "Nanoscale Size Effect of Magnetic Nanocrystals and Their Utilization for Cancer Diagnosis via Magnetic Resonance Imaging," J. Am. Chem. Soc. 127(16):5732-5733, 2005.
Lopez-Lopez et al., "Stability of Magnetizable Colloidal Suspensions by Addition of Oleic Acid and Silica Nanoparticles," Colloids and Surfaces A: Physiochem. Eng. Aspects 264:75-81, 2005.
Yu et al., "Synthesis of Monodisperse Iron Oxide and Iron/Iron Oxide Core/Shell Nanoparticles via Iron-Oleylamine Complex," Journal of Nanoscience and Nanotechnology 6:2135-2140, 2006.

* cited by examiner

*Primary Examiner* — Frederick Krass
*Assistant Examiner* — Issaac Shomer
(74) *Attorney, Agent, or Firm* — Seed IP Law Group PLLC

(57) ABSTRACT

A method for providing nanoparticle clusters of controlled dimensions is described. The method involves an activation of individual nanoparticles and the subsequent interaction between activated particles to form a cluster.

30 Claims, 26 Drawing Sheets

NANOPARTICLE CLUSTERS AND METHODS FOR FORMING SAME

FIELD OF THE INVENTION

The present invention relates to clusters of nanoparticles, hereinafter referred to as nanoparticle clusters and particularly to methods useful in the formation of clusters of a predetermined size. In a preferred embodiment the invention provides for magnetic nanoparticle clusters. The invention also provides for the use of such nanoparticle clusters in medical applications such as drug release, as mediators for hyperthermia and as contrast agents for magnetic resonance imaging.

BACKGROUND

One of the major problems with the application of nanotechnology is that the properties of the materials depend sensitively of the size of the particles. It is very difficult to grow particles or particle clusters that are relatively monodisperse (one size only). It is also very difficult to grow structures that have selected sizes over a wide size range using a single process.

For example, in the field of MRI (magnetic resonance imagining), it is known to grow nanoparticle clusters for the production of contrast agents by simultaneous in situ growth and stabilisation of the nanoparticles in the presence of polymers (usually dextran) or polyelectrolytes. Such techniques are described, for example, in WO2005076938 which provides a description of multi-polymer-coated magnetic nanoparticle clusters, aqueous magnetic fluids comprising same, and methods of their use in separation procedures. The multi-polymer-coated magnetic nanoparticle clusters comprise a super paramagnetic core, with a first polymer attached thereto, which does not render the first polymer-super paramagnetic particle complex colloidally stable, and a second polymer attached thereto, which stabilizes the complex. Methods of separation, including separation of expressed protein from cells and viruses expressing the same are all described. Although the described method has the ability to provide a stable cluster, the size control of the formed clusters is determined by the surface chemistry of the stabilising polymer used and the larger clusters are essentially polymers with low nanoparticle content. It is therefore difficult to control the size distribution of the formed clusters.

In summary, using such known techniques, the size of the cluster finally obtained is process controlled as opposed to user controlled. It can therefore be difficult to generate samples of reproducible size. Additionally, a broad range of cluster sizes is obtained There is therefore a need for a methodology that will enable a production of nano-sized objects formed from different materials and of a controlled size.

SUMMARY

These and other problems are addressed by a methodology in accordance with the teaching of the present invention that enables a production of nanoparticle clusters of a controlled size in a repeatable fashion.

Using the teaching of the invention, a methodology is provided that enables a growth in suspension of clusters of nanoparticles. The size of the final clusters chosen may be selected with some precision. Similarly, control over size distribution may also be exerted. Using methodologies in accordance with teachings of the present invention, it is possible to terminate the process when a required size has been achieved. Monitoring techniques may be employed to monitor the growth of the clusters in suspension to determine when the required size has been achieved. Using this technique it is also possible to control the polydispersity of the suspension.

Accordingly there is provided a method in accordance with claim 1. Advantageous embodiments are detailed in the dependent claims.

These and other features of the invention will be understood with reference to the following description and drawings.

BRIEF DESCRIPTION OF THE DRAWINGS

The present invention will now be described with reference to the accompanying drawings in which:

FIG. 14 shows polydispersity index (PDI) data and mean count rate in a BE experiment with sample H5a.

DETAILED DESCRIPTION OF THE DRAWINGS

Figure 1:
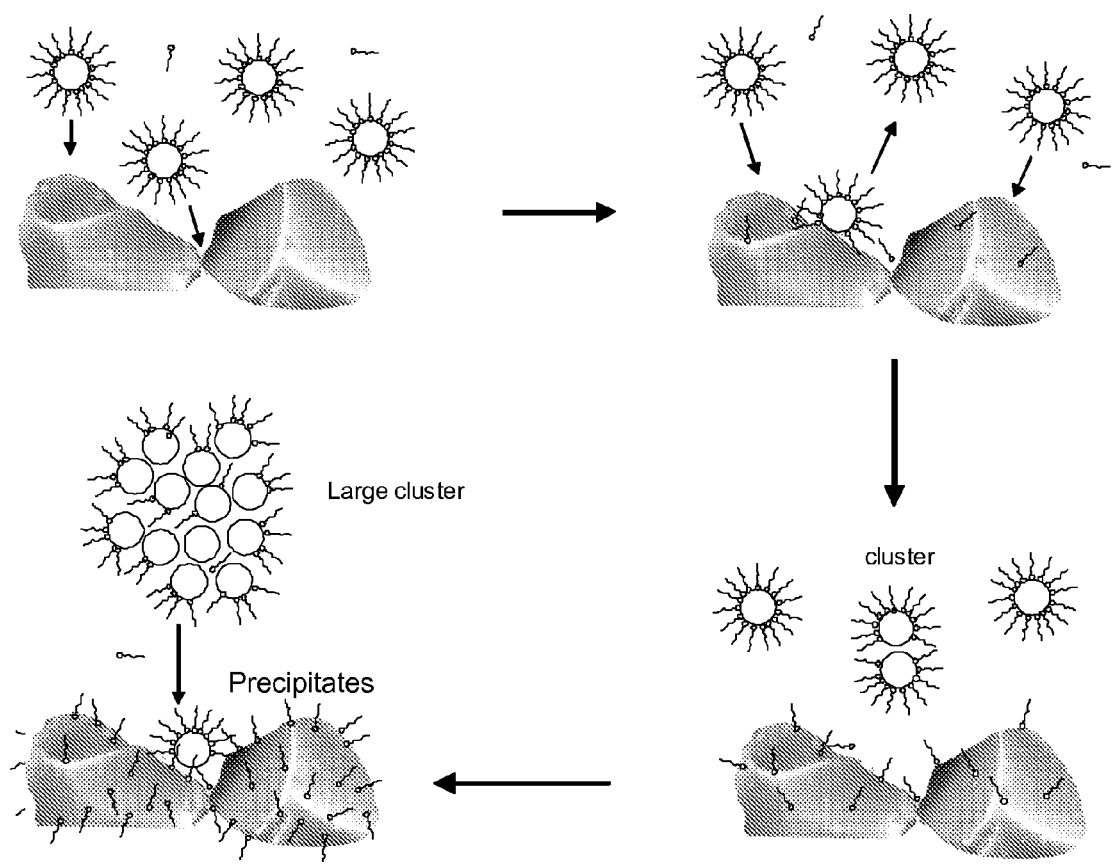
FIG. 1 is a pictorial representation of the steps involved in the preparation of nanoparticle clusters in accordance with an exemplary method according to the teaching of the invention.

The present invention will now be described with reference to exemplary embodiments which are provided to assist in an understanding of the teaching of the invention. Using the teaching of the invention, a methodology is provided that enables a growth in suspension of clusters of nanoparticles. The clusters are formed of a plurality of individual nanoparticles. The size of the final clusters chosen may be selected with some precision. Similarly, control over size distribution may also be exerted. Using methodologies in accordance with teachings of the present invention, it is possible to terminate the process when a required size has been achieved. Monitoring techniques may be employed to monitor the growth of the clusters in suspension to determine when the required size has been achieved.

Within the context of the present invention nanoparticles in suspension are exposed to an activation source which serves to stimulate the combination of two or more individual nanoparticles to create a nanoparticle cluster. The source of activation could be an activation substrate or indeed other activated particles or already formed clusters within the suspension. It does normally require for the activation source to be a material which provides an activation surface. By removing the suspension from the source of activation it is possible to terminate the further growth of the nanoparticle clusters. In this way a judicious selection of the appropriate time for removal can be useful to provide nanoparticle clusters of a determinable size and distribution.

Thus for example, the growth can be monitored and once clusters of a required size are obtained, then the further growth of the clusters can be restricted by removing the suspension from the contact with the activation source. In this way it is possible for the user to select the final dimensions of the clusters provided. In effect, the control of the dimension of the growth of the nanoparticle clusters is maintained through interaction between the nanoparticles in the suspension and the source of their activation.

In one embodiment the source of activation is a substrate such that the interaction is between the nanoparticles in the first phase (the liquid phase) and the activating substrate in the second phase (the solid phase). One suitable substrate that may be utilised is a silica substrate. It will be understood that within the context of the present invention that the term silica is intended to include both pure silica ($SiO_2$) and other naturally occurring forms of silica which, as will be understood by the person skilled in the art, includes impurities in the form of one or more trace elements. One particularly useful form of silica is alkyl chain grafted silica, another is cyanated silica.

In another embodiment the source of activation is another activated particle or cluster within the suspension. Such an arrangement is particularly useful in the context of seeding a suspension with already activated particles or clusters to enable continued growth of clusters within that suspension or indeed where a continuous cycle of formation of clusters is desired, and the number of activatable particles in the suspension has been diminished through the formation of clusters.

Initially the nanoparticles are stabilised through provision of a plurality of capping agents on the nanoparticle. It will be appreciated that the choice of capping agent selected will have to be made based on the capacity of the capping agent to bind onto the surface of the nanoparticle so as to stabilise the nanoparticle. The capping agent is subsequently at least partially stripped from the nanoparticle. The stripping of the capping agent changes the stability of the nanoparticle such that it is now reactive. The stripping may be effected through provision of an activating material such as a substrate that exhibits an affinity for the capping agent. Interaction between a capped nanoparticle and the activating agent initiates the stripping. Subsequent to their formation, reactive nanoparticles combine with one another to effect generation of nanoparticle clusters—i.e. two or more nanoparticles which are chemically of physically linked to one another.

Figure 2:
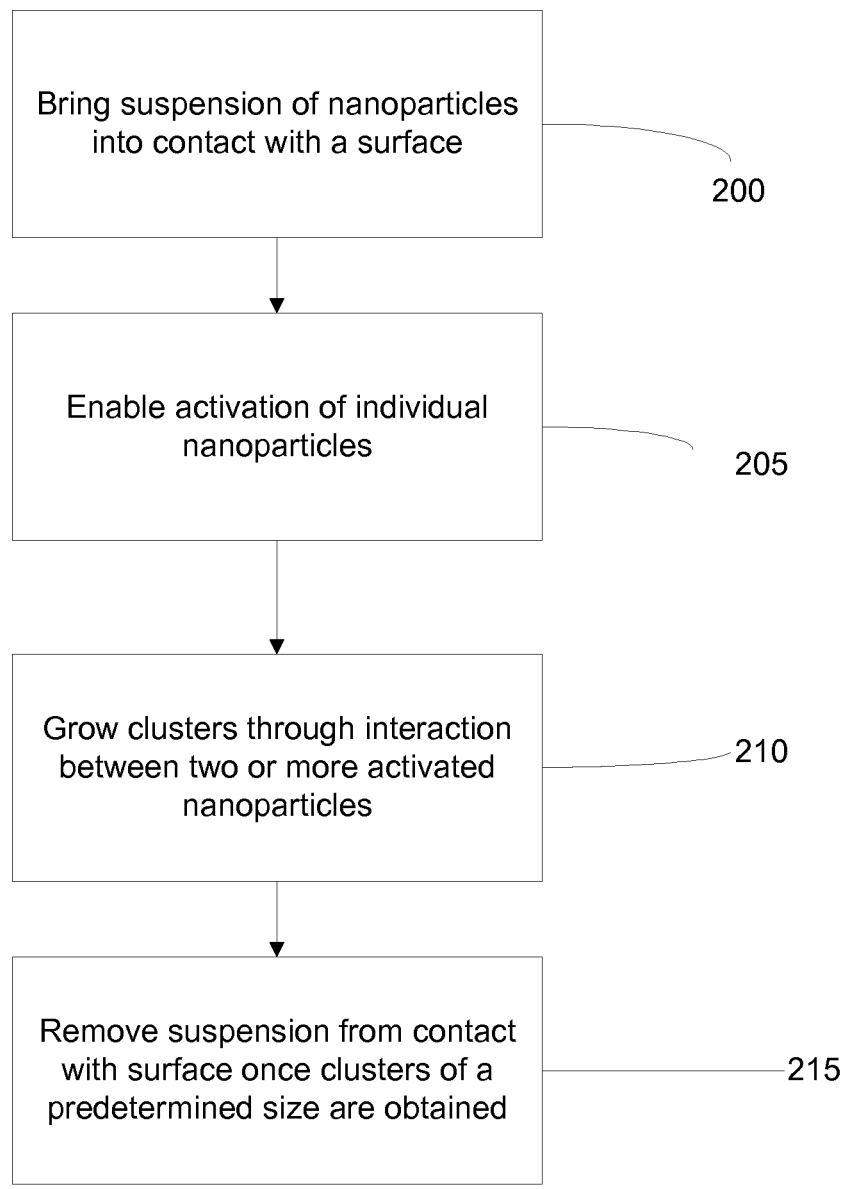
FIG. 2 is a schematic showing such steps associated with the representation illustrated in FIG. 1.

As shown in FIGS. 1 and 2, a methodology in accordance with the teaching of the invention is based on an understanding that bringing a suspension of dispersed nanoparticles into contact with an activating source such as a surface may lead to the growth of clusters of the nanoparticles. The contact with the surface leads to a gradual aggregation of individual particles into clusters. The longer the particles in suspension are maintained in contact with the surface, the larger the final size of the obtained cluster. In this exemplary method, a user can terminate the interaction between the two once clusters of a desired size are predominant. Alternatively, a portion of the suspension could be removed, allowing the remainder to continue the process of nanoparticle cluster growth.

In this illustrated example of a mechanism that may be considered as driving the interaction, a suspension of nanoparticles are brought into contact with a surface (Step 200). Through interaction with the surface, individual particles of the plurality of available particles in the suspension become activated through a loss of surfactant molecules on desorption from the surface (Step 205). Two or more of these activated particles combine, leading to the growth of clusters (Step 210). A repeat of this interaction between activated particles results in larger clusters which may precipitate from the suspension (Step 215). Both the primary particles in the suspension and/or the formed clusters have an affinity for the surface and in this exemplary embodiment where the substrate is provided below the suspension, precipitation from suspension may be on-going throughout the process. In this way, there is ongoing loss of material from the suspension. Once the clusters of useful dimensions are found then it is possible to remove the suspension, with those clusters, and then retrieve or stabilize the clusters.

Effectively, in this illustrated embodiment, a contact between an individual nanoparticle which is in suspension with the surface of the substrate activates the previously stabilized nanoparticle which may then combine with a similarly activated particle. It is also possible, within the suspension, that activated particles can activate unactivated or stabilized particles. It is thought however that a dominant source of activation, where there is an activating substrate, is the activating substrate. As the growth of the cluster is dependent on activation of the nanoparticles, it is time dependent. As a result, the process may be controlled. This control may be effected by either monitoring the process through a sampling method and terminating the process when the sampled distribution size meets predetermined requirements or, assuming that after a predetermined time that a predetermined size distribution has been achieved and using time as the terminating factor.

Initial experimentation has been based on a use of heptane suspensions of fatty-acid coated monodisperse (single sized) 10 nm iron-oxide nanoparticles. These nanoparticles were synthesised in a fashion that will be apparent to the person skilled in the art, such as using the techniques disclosed in *Size-controlled synthesis of magnetite nanoparticles*, Sun S. H., Zeng H., Journal of the American Chemical Society, 124 (28), 8204-8205, 2002. These suspensions are known to be stable and unchanging for many months. In effect these coated nanoparticles form the primary particles within the process and have a core with a coating or capping agent provided on the surface thereof, the coating being activatable, which will result in an activated nanoparticle. However in the initial suspension the nanoparticles are provided in a stabilized form, the stabilization being provided by the capping agent on the surface of the individual nanoparticles.

To activate the nanoparticles, the suspensions were placed over a C18-grafted silica substrate in a standard cuvette. The size of the suspended particles were then monitored by photon correlation spectroscopy, PCS. The particles were observed to gradually increase in size, due to aggregation, or clustering, of the primary particles.

Figure 1A:
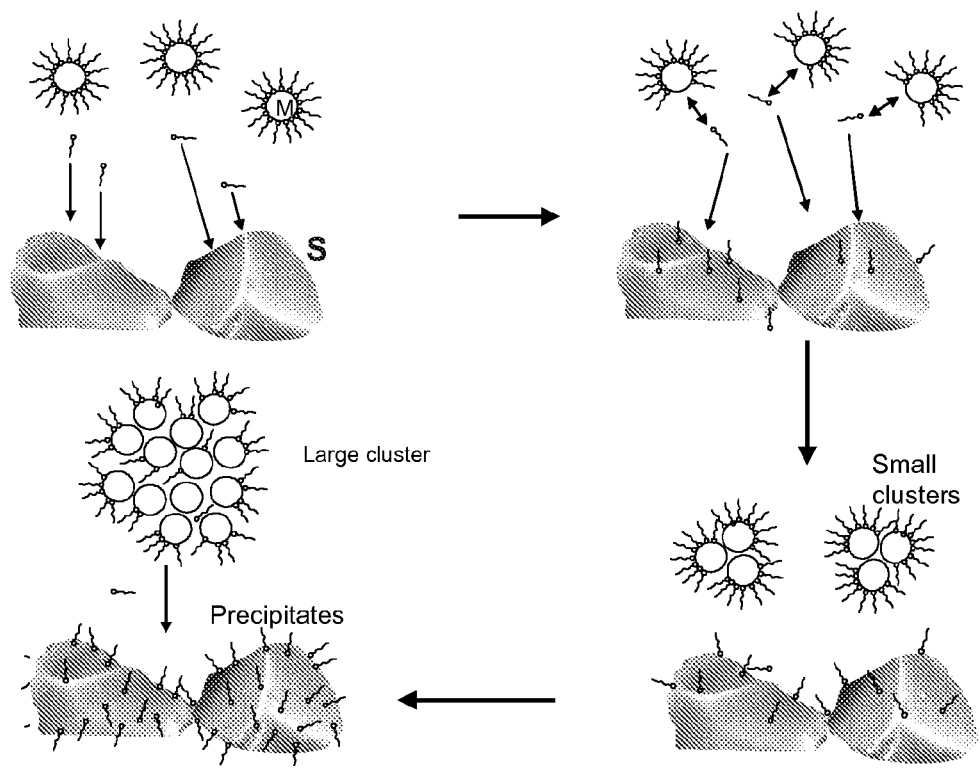
FIG. 1a is a pictorial representation showing an alternative mechanism for provision of nanoparticle clusters in accordance with the teaching of the invention.

While the above described mechanism of surface activation of individual ones of the nanoparticles within the solution suspension is beneficial in that it provides an explanation of a suitable mechanism through which reactive nanoparticles may be generated, it will be understood that it is not intended to limit the teaching of the present invention to any one specific mechanism except as may be deemed necessary in the light of the appended claims. To support this position, FIG. 1a illustrates an alternative mechanism through which interaction between the nanoparticles, the suspension and the substrate may result in the gradual aggregation of individual nanoparticles to form nanoparticle clusters. It will be appreciated from a review of the schematic of FIG. 1a with reference to FIG. 2, that the language of FIG. 2 continues to support the general mechanism of how interaction between a suspension of primary nanoparticles within a stabilizing suspension and an activating substrate can provide for controlled growth of nanoparticle clusters As shown in FIG. 1a, there is an additional pathway for nanoparticle cluster activation, which does not involve the direct interaction of the particle with the silica, as was previously described with reference to FIGS. 1 and 2. In this indirect mechanism, the substrate is again formed from silica and the nanoparticles are provided in a suspension of oleic acid which assists in maintaining the nanoparticles in a stable form. As was described with reference to FIG. 2, in step 200, the suspension is brought into contact with the silica substrate. In the direct mechanism of FIG. 1, the silica interacted directly with the nanoparticles whereas in this indirect mechanism the silica slowly strips the suspending medium of oleic acid which is the surfactant on the primary nanoparticles. The stripping of this surfactant which has provided the stability previously evident in the primary nanoparticles effects the generation of reactive nanoparticles within the suspension (Step 205) and results in cluster growth through interaction of two or more reactive nanoparticles (Step 210). This cluster growth further shifts the equilibrium between free surfactant in the suspending medium and nanoparticle-adsorbed surfactant, so that some surfactant desorbs creating active nanoparticles with incomplete surfactant layers, resulting in cluster growth. Once the clusters have reached a predetermined size it is possible to terminate the growth of clusters by removing the suspension from contact with the activating substrate (Step 215).

The validity of this second mechanism has been demonstrated by growing clusters in a suspension where the primary nanoparticles were prevented from direct access to the silica surface, and yet cluster growth resulted. It will be appreciated that the direct mechanism of FIGS. 1 and 2 or the indirect mechanisms of FIGS. 1a and 2 are not mutually exclusive.

Irrespective of the mechanism, by changing the amount of substrate available or by increasing the ratio of the stabilizing surfactant or capping agent to the nanoparticles, it is possible to demonstrate that the rate and extent of growth, and the width of the cluster size distribution, may be controlled, and indeed that the growth may be terminated. Either of these two factors achieve the necessary stabilization of the existing reactive nanoparticles and prevent formation of new reactive nanoparticles. In the scenario where the activating substrate is removed, no further activation can be effected. Similarly, by having an excess concentration of the stabilizing surfactant (for example oleate) in the suspension, the surfactant molecules will bind to any reactive nanoparticles thereby stabilizing them before they interact with other reactive nanoparticles and/or prevent formation of new reactive nanoparticles by blocking activating sites on the substrate.

Figure 3:
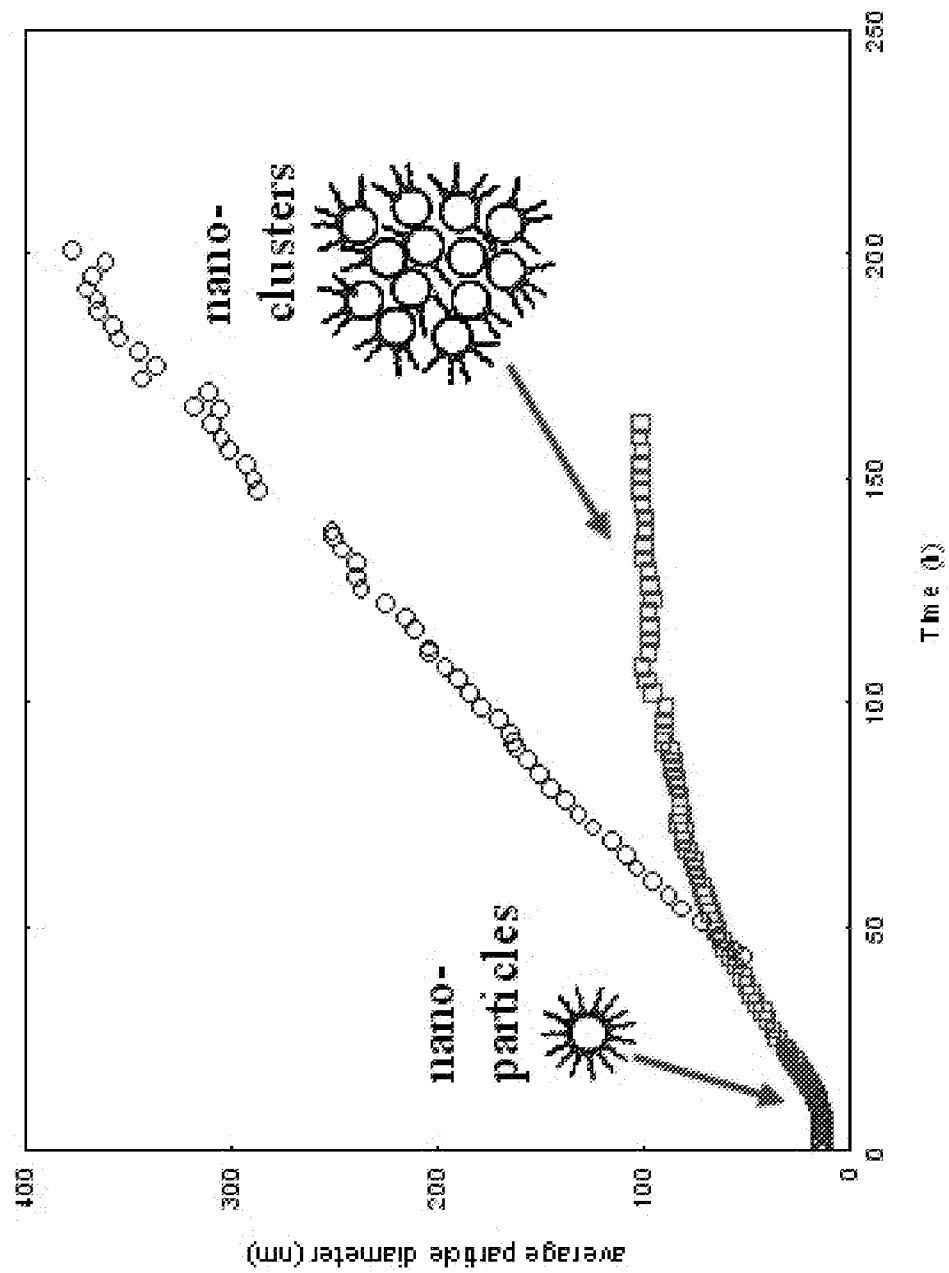
FIG. 3 shows data from two typical PCS experiments with different ratios of nanoparticles to silica surface, the results demonstrating control over the rate of growth

FIG. 3 shows data from two typical PCS experiments with different ratios of nanoparticles to silica surface. The results demonstrate control over the rate of growth and that the cluster size may be selected in a range from 10 to 400 nm, by simply removing the suspension from the silica substrate at the appropriate time. Experiments have also been performed that demonstrate that it is possible to grow the clusters off-line and to monitor their growth by taking samples intermittently for PCS. Hence the volume of a sample for reaction is not limited to the volume of a cuvette (c. 4 ml). In this way it will be understood that a technique in accordance with the teaching of the invention enables a continuous monitoring of the process in order to allow the user to select an appropriate time to terminate the interaction between the particles in suspension and the substrate.

Figure 4:
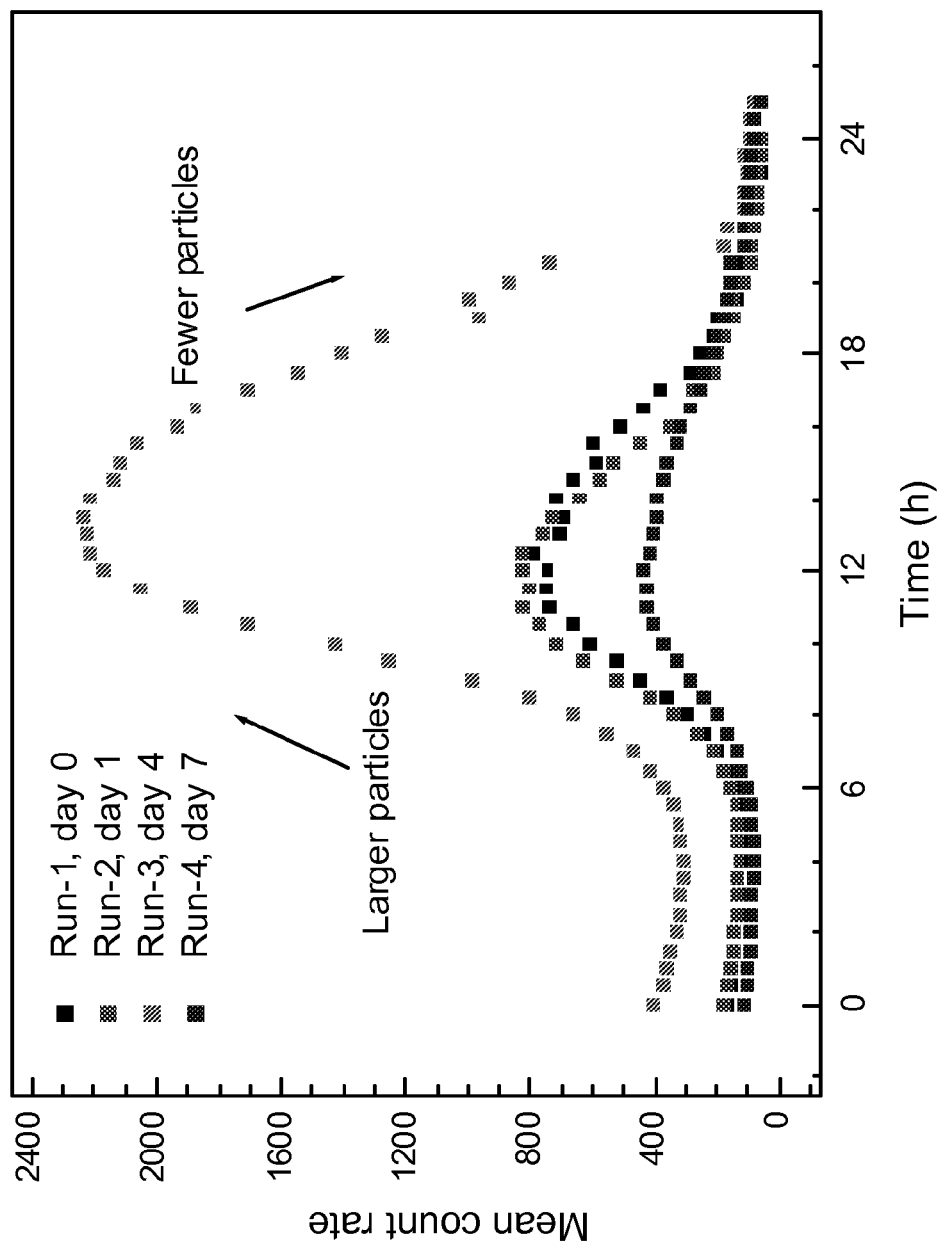
FIG. 4 shows data recorded for a different series of preparations, providing further confirmation that the clusters grow by the addition of nanoparticles from the suspension.

FIG. 4, recorded for a different series of preparations, provides further confirmation that the clusters grow by the addition of nanoparticles from the suspension. Initially as larger clusters scatter light more strongly, the intensity of scattered light increases. However as the process continues, eventually there are fewer clusters present and the scattering intensity decreases.

It will be appreciated that a methodology that enables a control of cluster size has many advantages. This capability may for example be used in biomedical applications where a particular size or range of sizes is required. Thus the suspensions may be particularly useful as contrast agents for magnetic resonance imaging, and as mediators in hyperthermia. These applications are particularly suitable because clusters can accumulate in specific sites due to their physical size. Once in situ, they may be detected (as in the case of MRI) or if the formed nanoparticle clusters have magnetic properties may be stimulated to produce heat (for hyperthermia applications). In this context it will be appreciated that the actual dimensions of the clusters are important for effectiveness. Using clusters formed in accordance with the teaching of the invention therefore may be considered as extremely effective in that their size and distribution of size is controllable.

In this way, the provision of particles of a controlled size should improve the physical targeting of the particles, which as mentioned above may allow a targeting of specific structures for MRI, e.g. the leaky vasculature of tumours. Furthermore, as the same methodology can be used to produce different sized nanoparticle clusters, it may be possible to develop agents that target more than one disease. For instance, it is known that leaky vessels are also associated with autoimmune diseases, including arthritis. Within this context drug delivery or drug targeting within the context of the present invention is based on an understanding that particles in the body are rapidly recognised and attacked by the macrophages (white blood cells) and processed by the reticuloendothelial system. The blood circulation time can be increased by using smaller particles (<50 nm is good) and/or generating what is termed stealth particles by for example grafting masking molecules such as polyethylene-glycol onto them. These particles will circulate many times and accumulate anywhere that they have a specific chemical interaction (e.g. if they are coated with an antigen and the antibody is present), or a physical preference. Thus sub-100 nm particles eventually accumulate in the leaky vasculature of tumours (if present). This physical accumulation is essentially a passive process and while the word targeted suggests a more active direction of the specific drug to an area of interest it is sometimes used to describe this passive process. By using particles formed using the techniques of the present invention it is possible to ensure that the main size distribution of the particles being used falls within the required parameters for effectiveness.

As mentioned above, another advantage, which is specific to clusters formed using suspensions of magnetic nanoparticle clusters such as iron oxide, is that they can be stimulated by applied alternating magnetic fields, resulting in rapid localised heating or hyperthermia. Hyperthermia procedures depend upon mediators that can localise in, or be introduced to, the tumour, and which have a large specific absorption rate (SAR). Materials formed in accordance with the teaching of the invention are very suitable for such applications, as their large size will aid in physical targeting, but the small primary nanoparticle size (c. 10 nm) ensures a very high SAR at tolerable magnetic field strength and frequency. By the term tolerable is meant tolerable to the body in which the particles are embedded and which is being targeted. Using nanoparticle clusters in this way is particularly effective in providing the localised heating that is useful in the treatment of primary cancers where the heating of the site is used to destroy the cancerous tissue.

Other ways to induce activation or localised heating of an embedded nanoparticle are to use RF fields or indeed laser triggering.

The ability to provide for controlled generation of nanoparticle clusters of a predetermined size is particularly useful in the context of creating effective mediated drug release agents. As the dimensions of the agent can be controlled its eventual target site within the body may also be confidently selected. In this way thermo-sensitive liposomes having nanoparticle clusters provided therein or polymeric coated nanoparticle clusters may be useful in drug sequestering and controlled release of the drug to a target site within the body. The liposome or polymer may be used to provide a matrix within which a particular drug or pharmaceutical composition is loaded. By encapsulating nanoparticle clusters within such a matrix and then introducing that combination into the body it is possible to deliver the pharmaceutical composition to the desired target site. By suitably heating the magnetic nanoparticle clusters, the encapsulation combination is disrupted and the composition released to the surrounding tissue. As the methodology of the present invention enables the formation of nanoparticle clusters of known dimensions, a fluid formed from such a drug delivery unit, has components of a controlled dimension and as such the ultimate destination of the components of that fluid within the body is determinable in a fashion that heretofore was not as known. The heating of the nanoparticle clusters may be effected in a number of suitable manners such as application of a magnetic or RF field, or indeed the targeting of the site where the drug delivery agent is located with a laser.

Another possible application of nanoparticle clusters formed in accordance with the teaching of the invention includes the formation of catalytic surfaces. Catalysts require a high surface area to volume ratio. Nanoparticle clusters of for example metal oxide materials prepared by this process and deposited on a solid substrate would have high surface area to volume ratios and so may be usable catalysts (e.g. in catalytic converters). Most applications would require removal of the capping agents (fatty acids), but this could be achieved by heating them as part of an annealing step which would also serve the purpose of fixing the nanoparticle clusters to the substrate. Clusters formed using the techniques of the invention would be formed of very monodisperse primary particles and could therefore be considered as providing excellent catalytic properties.

The formation of such complex structures is predicated in having formed the initial nanoparticle clusters. As discussed above, the methodology of the present invention creates the clusters within a suspension. Once the desired size of nanoparticle clusters is obtained, stabilisation of the clusters may be effected. It will be understood that a number of different mechanisms for stabilisation of nanoparticle clusters may be utilised, and it is not intended that the present invention be limited to anyone specific mechanism. Nevertheless examples of possible approaches will now be described which are based on a cross-linking and phase transfer of the nanoparticle clusters from suspension in an organic solvent into a stable aqueous suspension. It will be understood that these exemplary techniques are based on a magnetite based nanoparticle provided in an organic solvent, and it is not intended to limit the invention to such an arrangement. For example as will be understood from the gold nanoparticle cluster arrangement described hereinafter, the clusters are formed in a water suspension which may not require additional treatment.

One example of an approach for cross-linking includes exploiting the methods for olefin based polymerisations described by Hatton and Laibinis, ["Polymerization of olefin-terminated surfactant bilayers on magnetic fluid nanoparticles", Shen L. F., Stachowiak A., Hatton T. A., et al., Langmuir, 16(25), 9907-9911, 2000] the content of which is incorporated herein by way of reference.

Alternative techniques include those large number of aqueous phase transfer procedures which are based on the partial or complete displacement of alkyl capping agents from the surface of the nanoparticles by water soluble surfactants that form stronger bonds to magnetite. There are many reagents available for this, amongst those recently published describe the use of 2,3-dimercapatosuccinic acid phase transfer reactions to produce stable aqueous nanoparticle cluster suspensions. Examples of these include 1. "In vivo magnetic resonance detection of cancer by using multifunctional magnetic nanocrystals", Huh Y. M., Jun Y. W., Song H. T., Kim S., Choi J. S., Lee J. H., Yoon S., Kim K. S., Shin J. S., Suh J. S., Cheon J., J. Am. Chem. Soc., 127(35), 12387-12391, 2005. 2. "Nanoscale Size Effect of Magnetic Nanocrystals and Their Utilization for Cancer Diagnosis via Magnetic Resonance Imaging" Young-wook Jun, Yong-Min Huh, Jin-sil Choi, Jae-Hyun Lee, Ho-Taek Song, Sungjun Kim, Sarah Yoon, Kyung-Sup Kim, Jeon-Soo Shin, Jin-Suck Suh, and Jinwoo Cheon J. Am. Chem. Soc., 127 (16), 5732-5733, 2005.]

An alternative method could involve reacting the preformed clusters with aqueous polyelectrolytes, including polystyrene-sulphonate or one of the many poly(alkyl-cyanoacrylate)s. This approach, it will be appreciated, may result in stabilisation of the clusters and rendering them water soluble in one step.

It will be understood by the person skilled in the art that the methodology in accordance with the teaching of the present invention utilises a process of adsorption which involves separation of an atom, molecule, or particle from one phase accompanied by its accumulation or concentration on the surface of a second phase, in this example a silica substrate. Physical adsorption is caused mainly by van der Waals and electrostatic forces between adsorbate molecules and the atoms/molecules on the adsorbent surface. Thus adsorbents are characterised by surface properties such as surface area and polarity. A large specific surface area is preferable for providing adsorption capacity. Porous carbon-grafted silica comes under the category of non polar adsorbents. These adsorbents have more affinity with oil or hydrocarbons than water. On the other hand, chemical adsorption involves the formation of chemical bonds between atoms on the adsorbed molecule and atoms on the surface of the second phase. It will be appreciated that within the context of the present invention that any type of adsorption that enables an activation of the suspended particles can be considered useful and it is not intended to limit the invention to any one example or constituent of any one example of a suitable adsorbent, indeed distinctly different types of adsorption are clearly present in the examples presented.

In the following paragraphs, experimental data is presented that is provided to demonstrate the effectiveness of the techniques that are in accordance with the teaching of the invention, and the underlying phenomena that supports this methodology. Such data is provided as exemplary results and it is not intended to limit the invention to any one set of experimental results.

The experimental data is based on an investigation into the interaction of a non-aqueous magnetite suspension with macroporous silica. Several types of silica surfaces were investigated including silica-C18 an octadecyl carbon loaded material, silica-CN (a negatively charged cyanated silica), and an untreated silica and an APS modified silica.

As mentioned above, the teaching of Sun et al show that nanocrystalline magnetite particles stabilised by a monolayer coating of oleic acid form a very stable suspension in non-polar solvents like heptane. The carboxylic head group is chemisorbed on the magnetite surface. The hydrophobic fatty chain extending from the magnetite surface is solvated by the nonpolar hydrocarbon solvent. There are many theories describing the mechanisms of stability of fatty acid coated magnetite in carrier liquids, and these will be apparent to the person skilled in the art. Within the present specification the term magnetite is used interchangeably with iron oxide, even though it is only one of a number of iron oxide phases that may be formed in the synthesis of magnetic nanoparticles. It is not intended to limit the invention to any one specific phase, and the term magnetite should be considered as encompassing the broad remit of any iron oxide.

EXPERIMENTAL

Materials

The substrate used in most of the experiments, silica-C18, was silica with 60 Å pores, 50 μm average particle size, and endcapping coated with C18 (Octadecyl, 6% carbon load) from Alltech Associates, Deerfield, Ill. Silica-CN a negatively charged cyanated silica, and an untreated silica of the same dimensions from the same source were also used.

The magnetite nanoparticles were synthesised by co-precipitation of mixed $Fe^{3+}/Fe^{2+}$ salts with ammonium hydroxide. A monolayer of surfactant coating was applied by adding excess oleic acid during the iron oxide precipitation. The magnetite dispersion was precipitated with acetone and methanol and washed five times with acetone and lastly with ethanol. The precipitate was then phase transferred into heptane. The heptane suspension was centrifuged at 13000 rpm (~16000 g rcf) for 40 min to remove any aggregated particles. Suspension H5a had a Z-average of 12.0 nm with a low PDI (0.09) and H5b had a Z-average size 11.8 nm Z-average and was also monodisperse PDI (0.07).

PCS Experiment

A calculated and predetermined quantity of magnetite suspension in heptane was placed over a silica substrate in the quartz cuvette for PCS analysis. The cuvette was placed in a PCS (Photon Correleation Spectroscopy) spectrometer with suitable care to avoid any agitation. The temperature of the cuvettes was maintained at 25° C. The quantity of silica was restricted so that the incident laser light was not occluded. In effect this limited the height of the silica to <1 mm, which is equivalent to 50 mg of silica.

In a first series of experiments a quantity of magnetic fluid sufficient to cover the entire silica surface with a monolayer of nanoparticles was placed over silica-C18 powder in a quartz cuvette. In a second series of experiments sufficient magnetite suspension was provided to produce a bilayer. The magnetite content was about 1.47 mM for sample H5a and about 1.52 mM for sample H5b. The following assumptions were made in calculating the quantities required:

There is no adsorption of nanoparticles into the pores on the silica-C18 surface.

The silica-C18 particles are spherical with diameter of 50 μm.

The adsorbed nanoparticles form a sheet of hexagonal closed packed spheres on the silica-C18 surface to form a uniform monolayer, and A bilayer is composed of two identical monolayers.

The onset of growth/aggregation of magnetite nanoparticles in suspension was monitored by PCS spectroscopy at an interval of 30 min for 1-7 days (as long as there were particles in suspension). The standard operating procedure (SOP) used for the PCS measurements was for 200 measurements with a suitable delay such that successive measurements are separated by 30 min. Each measurement takes about 5 min which, consists of 20 runs of 10 sec each. For most experiments the cuvette position and the attenuation index remain constant throughout the experiment as all the data collected was with one SOP (standard operating procedure). Therefore the backscattered light intensity is representative of the volume weighted number of scatterers.

Results

It was immediately apparent that the nanoparticles were adsorbing onto the silica. Irrespective of the concentration, the suspension lost colour over a period of hours, while the white silica-C18 powder turned a chocolate brown colour. In this way it can be understood that there is an interaction between the particles in suspension and the substrate.

Monolayer Equivalent Adsorption

Suspension H5a

Figure 5:
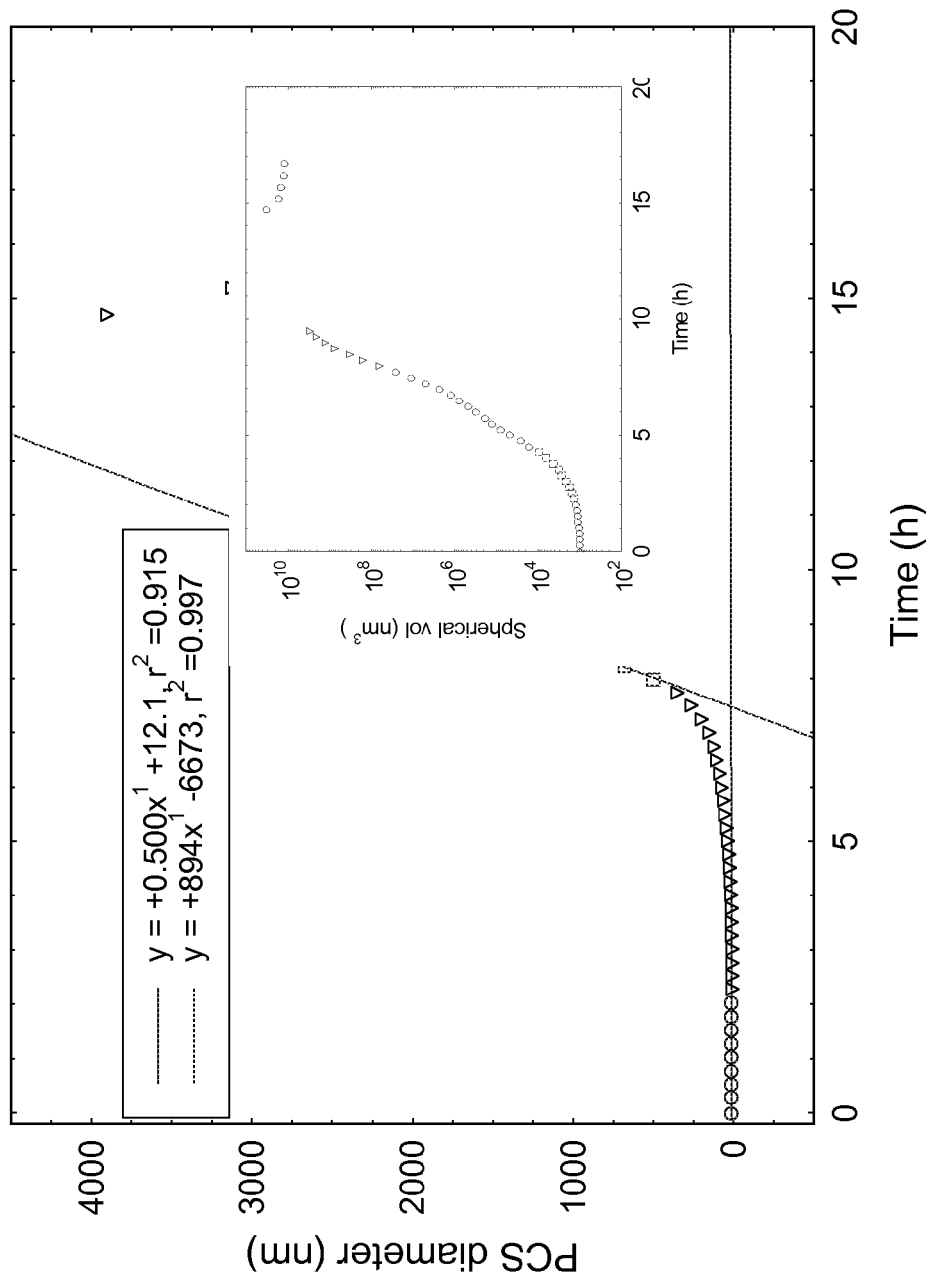
FIG. 5 shows PCS data for ME addition of magnetite suspension H5a over silica-C18 showing the increase in Z-average of suspension with time in run 1. The PCS diameter in the Y-axis is converted to the volume and shown as the inset.
Figure 6:
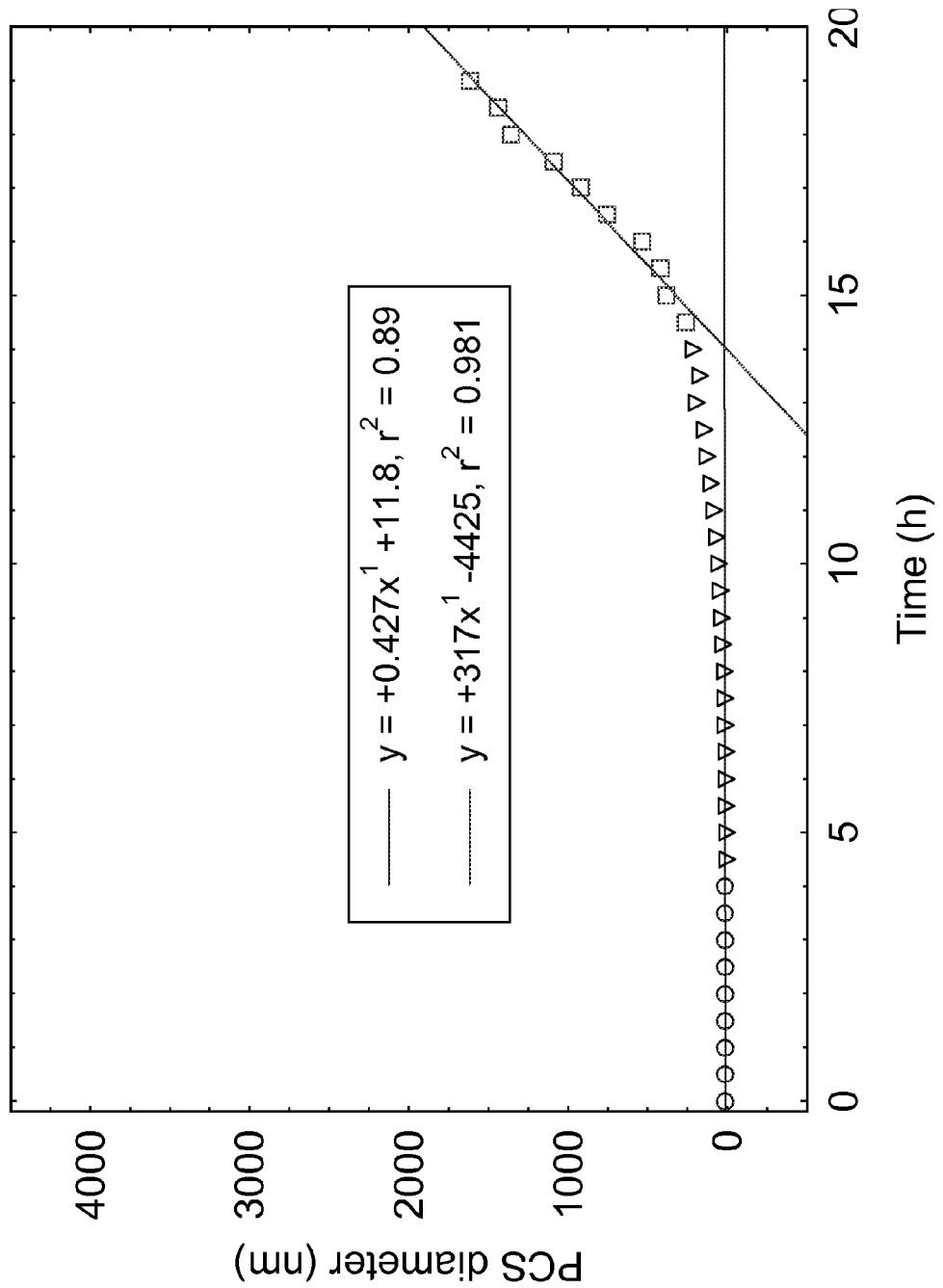
FIG. 6 shows PCS data for ME addition of magnetite suspension H5a over silica-C18.

In the first set of experiments one monolayer equivalent (ME) of magnetite suspension (H5a) was placed over silica-C18 and the Z-average particle size monitored over time, the data is presented in FIG. 5. The observed increase in size as a function of time shown in FIG. 5 is converted into change in spherical volume, and is shown as an insert in the figure. The growth of the clusters followed linear progress until about 2 hours in run 1 (FIG. 5), or until about 4 hours in run 2 (FIG. 6).

For both runs the initial linear growth phase was followed by a second more rapid linear growth phase. The smallest changes in the Z-average size of the particles are magnified in the volume curve, as volume is proportional to the cube of the radius. This would appear to indicate that, once a critical ratio of activated nanoparticles to non-activated nanoparticles are present within the first run and suspension, that the formation of the clusters can be accelerated. In this way it may be possible to seed certain suspensions with already activated particles to immediately progress to the second stage. It can therefore be understood that a suitable activation source for nanoparticles in suspension could include other nanoparticles or nanoparticle clusters within the same suspension. Such seeding of the suspension with already activated nanoparticle clusters or nanoparticles could be used therefore in certain applications to accelerate or maintain growth within that suspension.

Figure 7:
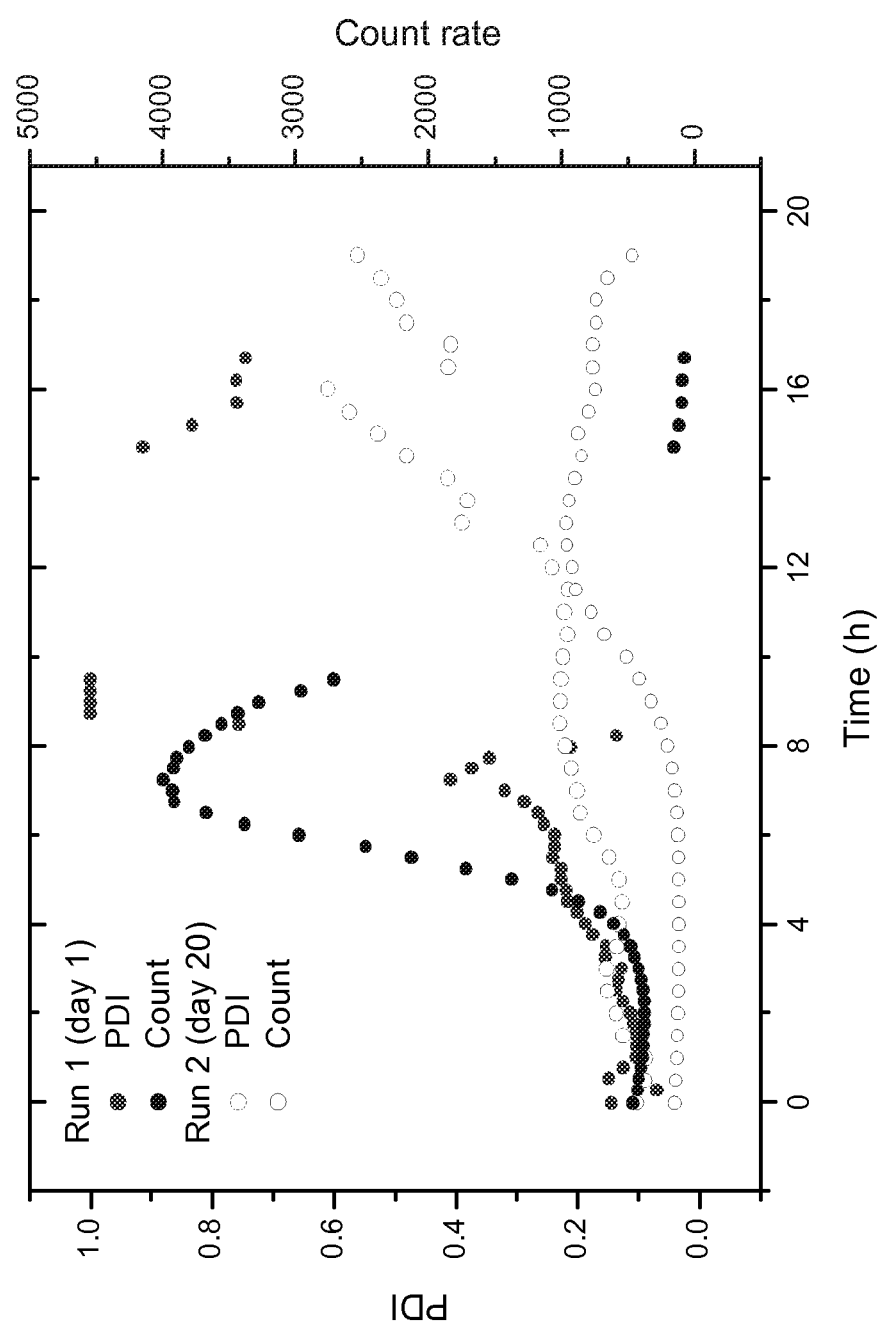
FIG. 7 shows the change of polydispersity index and the mean count rates for ME addition of magnetite suspension H5a over silica-C18 (for two runs, run 1 and 2).

The change in polydispersity index and mean count rate data for the two runs is presented in FIG. 7. The breaks in the data for the first run arose due to protocols on the acquisition PC interrupting the data storage. The polydispersity of the particles grew to a maximum (1.00) in about 7 hours during the first run where as the PDI did not exceed ~0.6 during the second run over the course of about 15 hours.

The mean count rates also increased drastically to 4000 kcps in just 7 hours in case of the first run. The two runs were performed under identical conditions, as far as possible, using the same magnetite suspension, but 19 days apart. Such information would indicate that certain implementations of the methodology of the teaching of the invention may require a monitoring of the size distribution as an indicator as to when is a suitable time to terminate the interaction between the suspended nanoparticles and their source of activation whereas other implementations may obviate the need for such monitoring by making assumptions that after a prescribed time period that a certain size distribution will have been realised.

Figure 8:
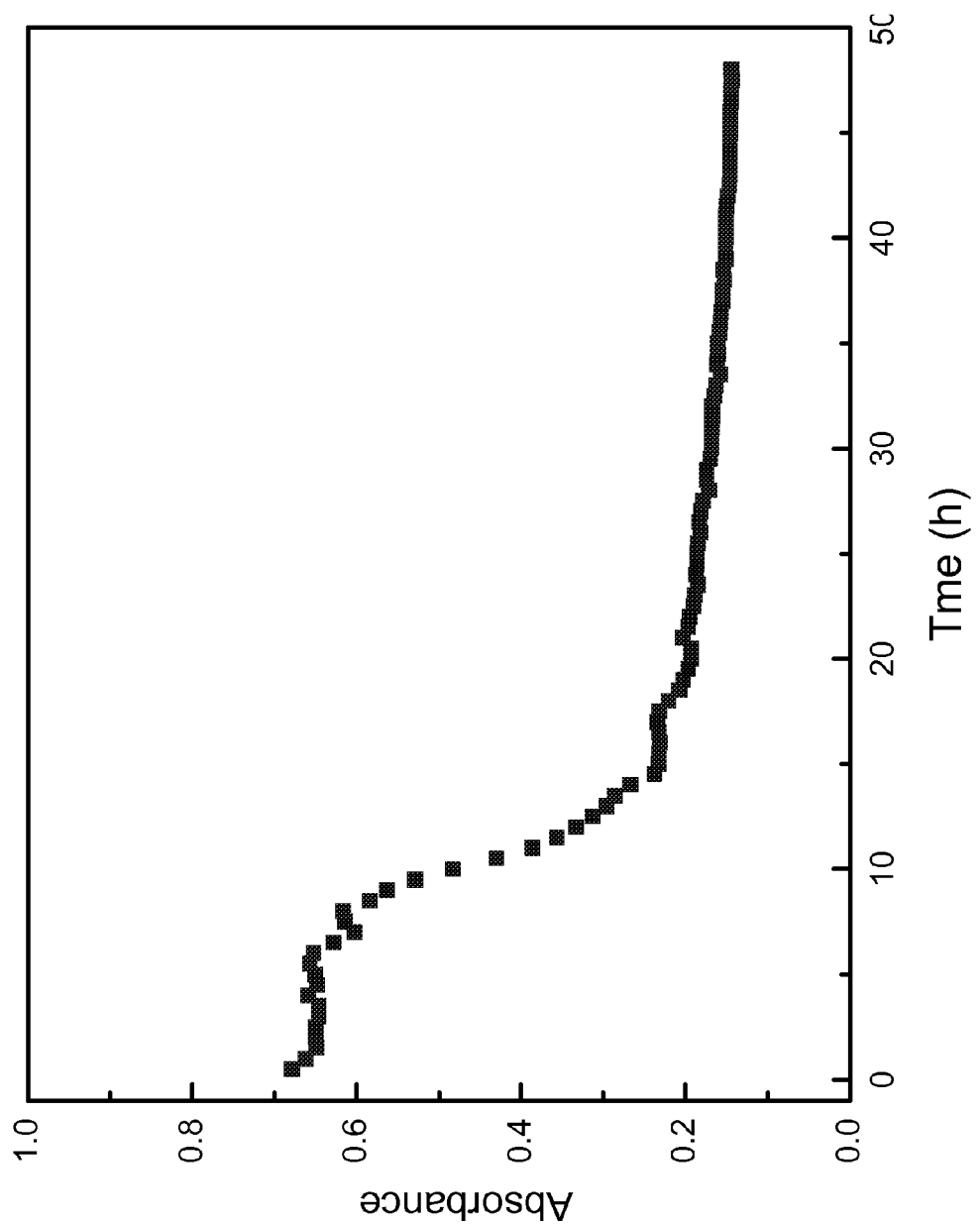
FIG. 8 shows UV absorbance at 475 nm over time for a ME experiment with H5a suspension over silica-C18.

The change in light absorbance of a ME magnetite suspension over silica-C18 was monitored over time, the data is presented in FIG. 8. The absorbance of light was recorded every 30 minute for 2 days, under conditions where the particles grew, when monitored by PCS. The changes in absorbance are synchronised with the growth pattern. There is very little change up to about 7-8 hours followed by a sharp fall in absorbance. The rate of change slowed significantly after about 15 hours and there was very little change in absorbance after 20 hours.

Suspension H5b

The ME experiment was also performed with an independently synthesised suspension, H5b, of slightly different particle size (12.0 nm). This experiment was repeated four times, the change in PCS size with time is given in FIG. 9.

Figure 9:
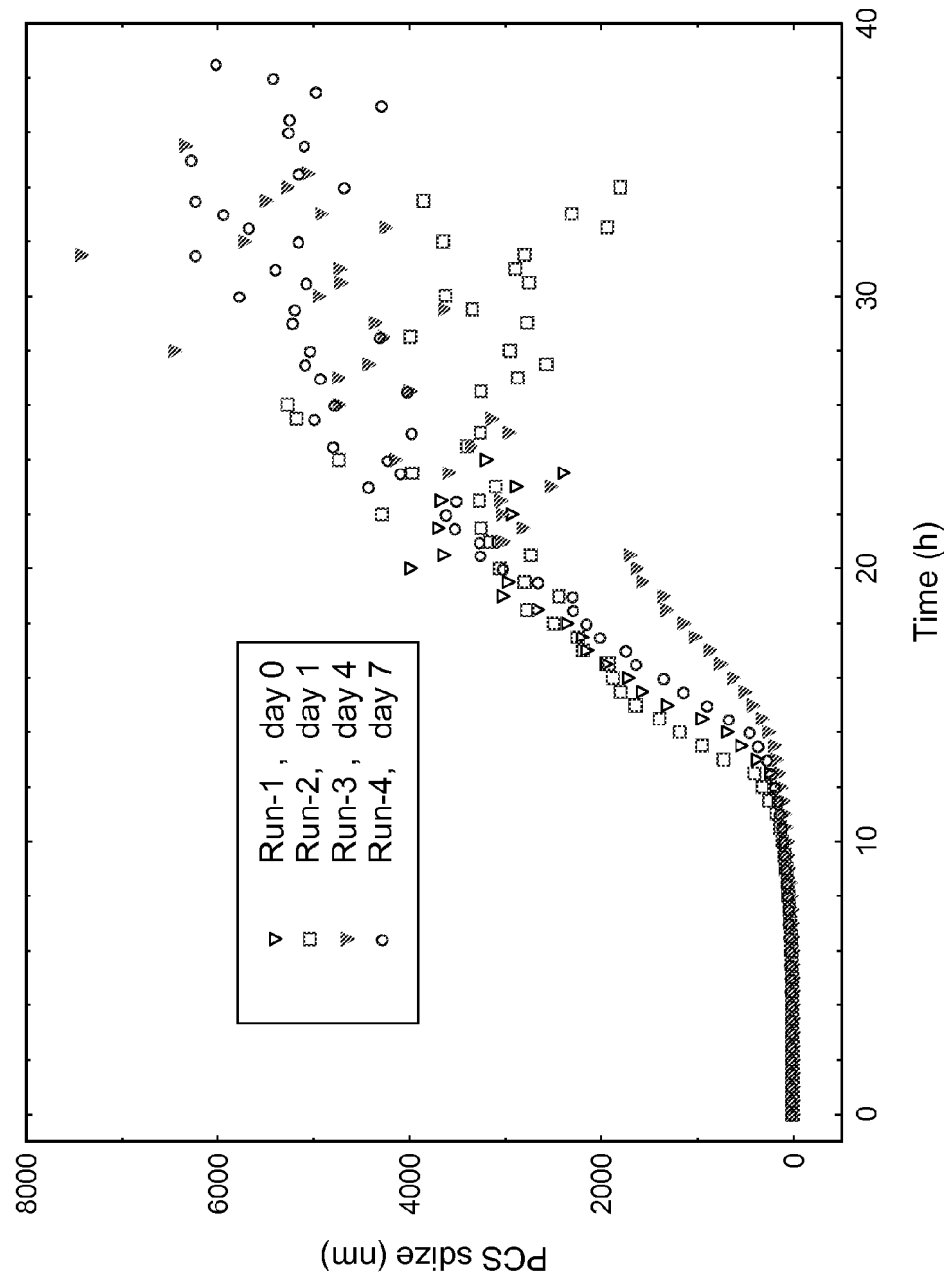
FIG. 9 shows Z-average size of H5b of slightly different size (11.8 nm) for ME addition experiment during 4 consecutive runs.
Figure 10:
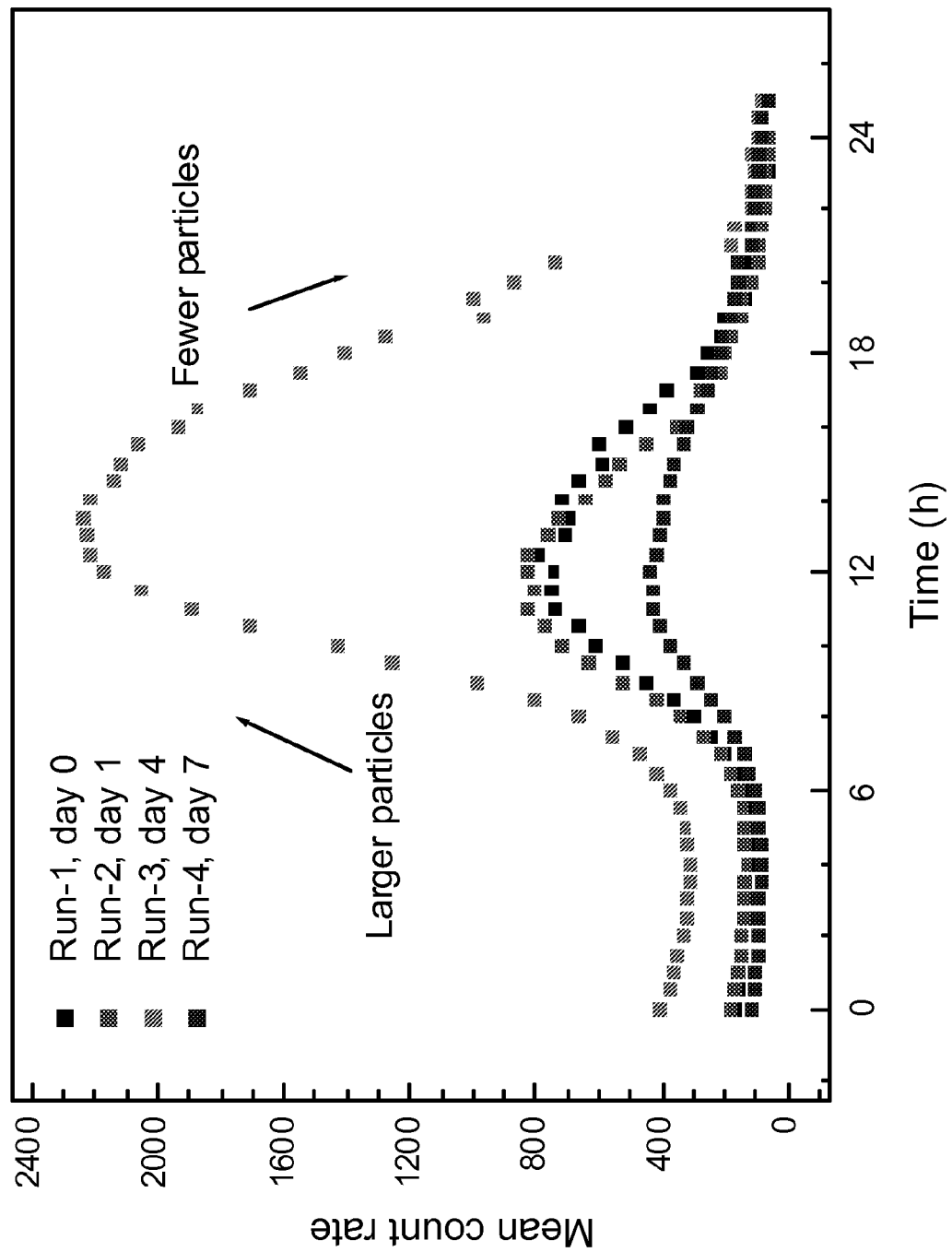
FIG. 10 shows the change in mean count rate with time for 1 monolayer addition of magnetite suspension (H5b) over silica-C18.

The change in mean counts for all the ME adsorption runs with suspension H5b are given in FIG. 10. The growth profiles of the particles are very similar for all four repeat experiments performed within 10 days from the date of synthesis of the magnetite suspension (FIG. 9). The pattern of change in PDI and counts (FIGS. 10, 11) is very similar to that observed for suspension H5a. The mean count rate in all the experiments increased steadily until ~12 hours, and then decreased to almost the starting value over another 12 hours. The variation in the value of the counts between runs is quite significant. However as the scattering intensity is weighted by volume a small change in the number of particles at the upper end of the size distribution, at any given time, will significantly affect the scattering intensity but not the z-average or PDI to as great an extent. The observation of a maximum is consistent with ongoing cluster growth and, as the experiment progresses, with the presence of fewer clusters. This is also apparent from the increase in the scatter of the particle size data after about 20 hours.

Figure 11:
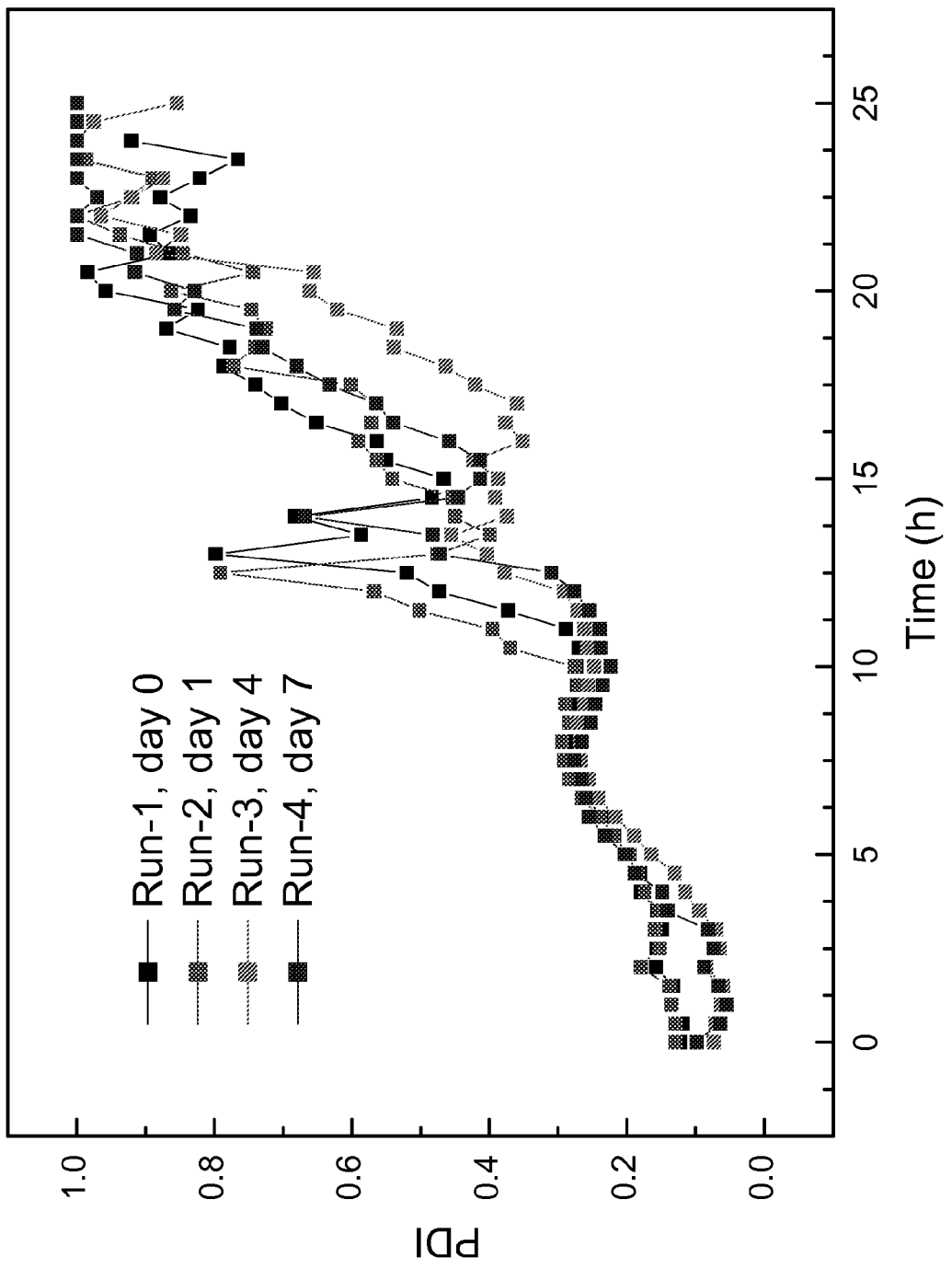
FIG. 11 shows the change in PDI with time for ME addition of magnetite suspension (H5b) over silica-C18.

The change in polydispersity index with time for is presented in FIG. 11. As the experiment progressed the PDI increased and the particle size distribution became wider. The mean count rate and the polydispersity index (PDI) show an interesting trend at 12-13 hours from the start, when the backscattered intensity is at a maximum. Around this time, an increase in PDI was seen in every experiment in the form of a spike.

Figure 12:
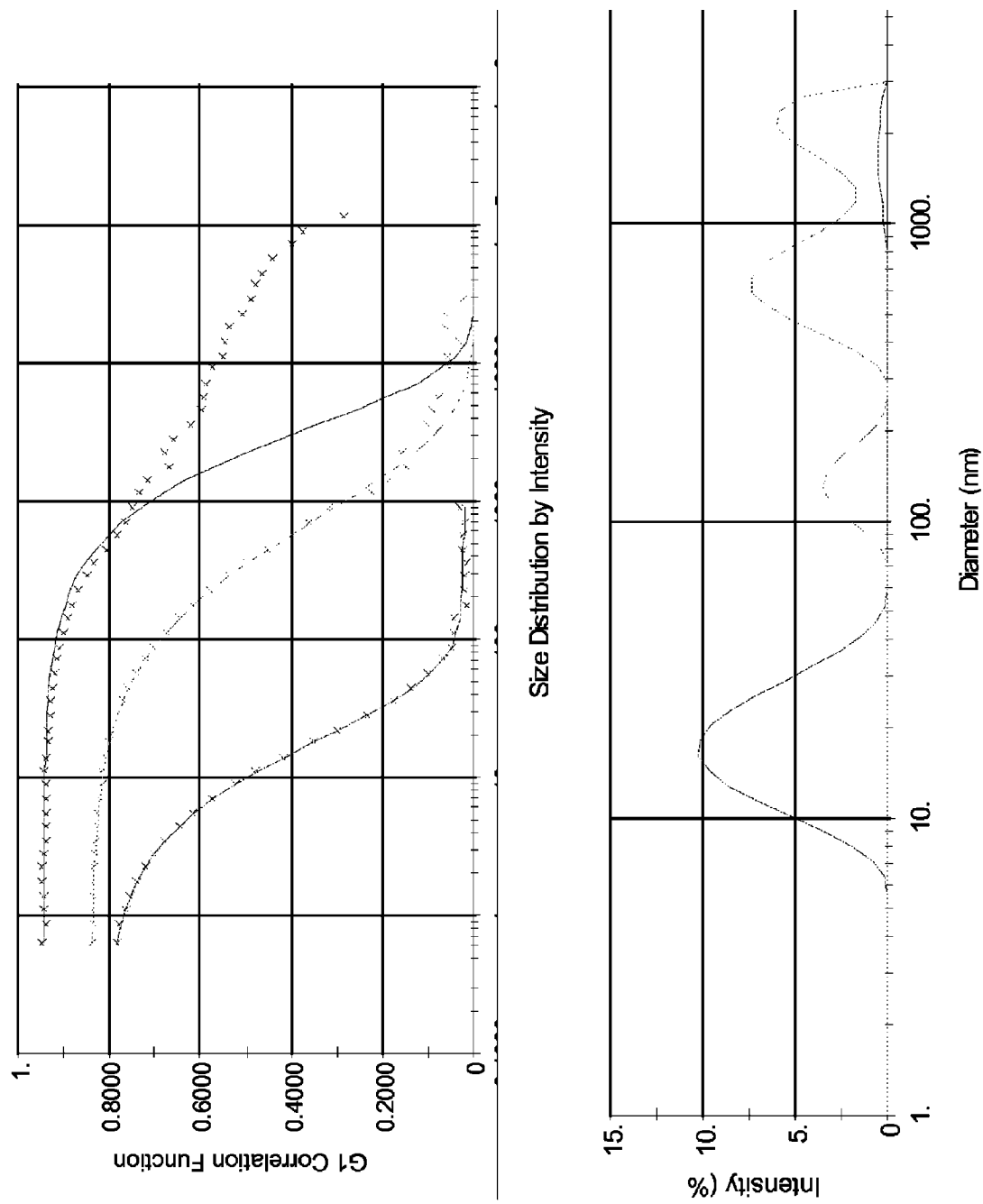
FIG. 12 shows PCS correlation data fits and the intensity size distribution for sample H5b in an ME experiment over silica-C18 after 5 hours (—), 13 hours (—) and at the end of the experiment 48 hours (—). The intensity distribution for the 48 hours (—) data is zero in the range shown; larger particles only present.

The correlation functions for three selected times are shown in FIG. 12. The quality of data fit is poorer for the later measurements. The PDI is high at ~12 hours, but there is still a good fit to the data, hence the Z-average may be considered a realistic average of the experimental distribution. The counts are highest in this region. But after about 24 hours the counts decrease to a small number. The fit in blue is only partly through the data points after 48 hours, hence the polydispersity index is 1.00, and the Z-average is a less reliable measure. The PCS software for all the ME experiments crashed, due to low scattering intensity, after 25-35 hours.

Bilayer Equivalent Adsorption

Figure 13:
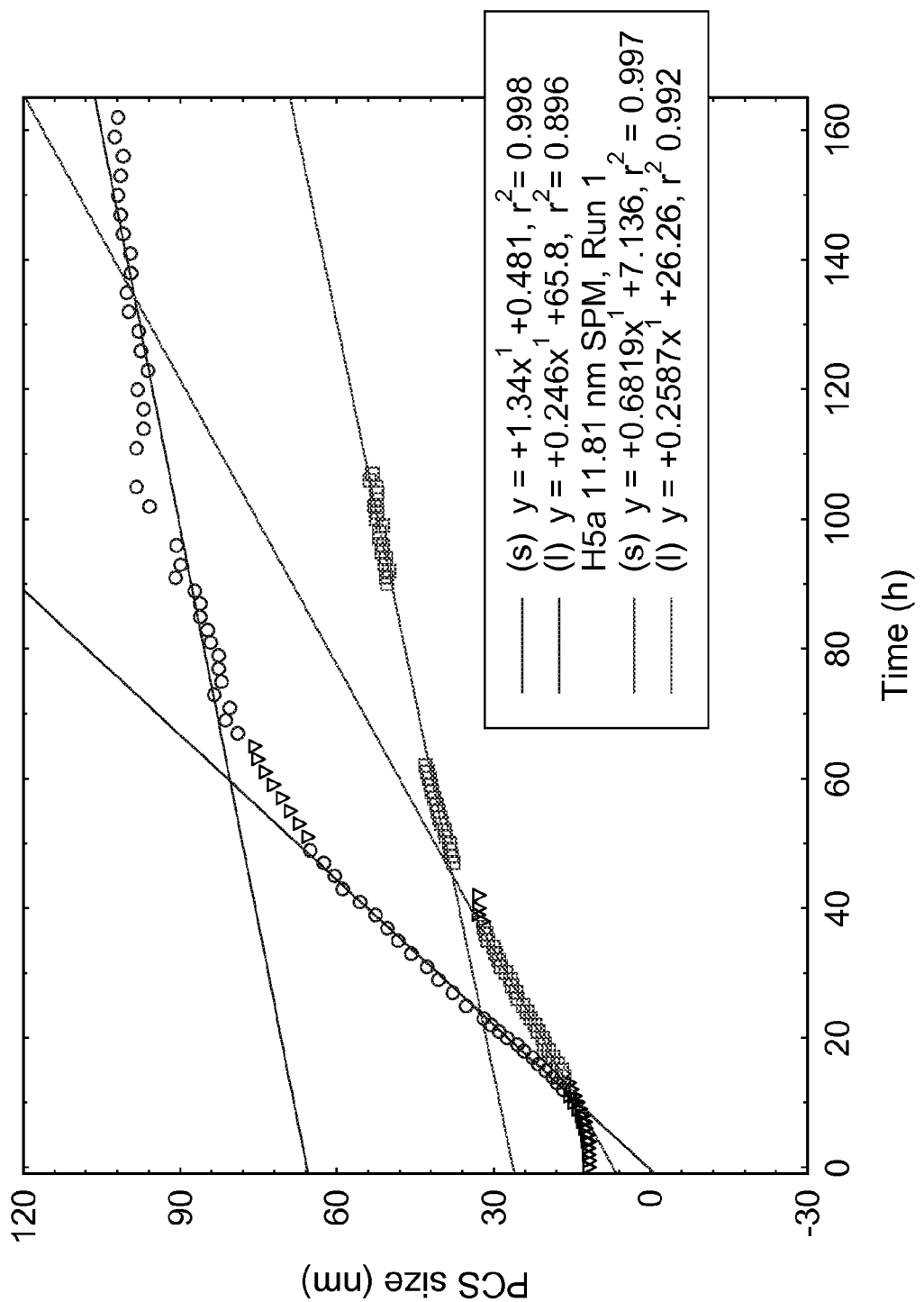
FIG. 13 shows PCS data for suspension H5a for BE addition over silica-C18 showing the increase in Z-average of suspension with time for run 1 (—), and for run 2 (—). The parameters for the linear fits to the short (s) and long (l) time data are included for each run.

The PCS data obtained for a bilayer equivalent (BE) adsorption of magnetite suspension H5a onto silica-C18, during run 1 and run 2 are presented in FIG. 13. The Z-average and PDI showed very similar behaviour to the ME experiments. There was a short linear growth phase up to about 4-6 hours for both the runs, which were carried out with a gap of 16 days using the same nanoparticle suspension. In contrast to the ME experiments, the BE suspensions follow two linear rapid growth phases. The first begins after ~15 hours and continues until 35 hours in run 1 and up to ~40 hours in case of run 2. The second linear growth phase showed almost identical growth rates, for both runs, of ~0.25 nm/hour.

It is interesting to note that in the ME experiment the PCS size increased to over 1500 nm in all cases, whereas in case of the BE experiments the growth was limited to about 100 nm. Based on this understanding, it is apparent that a specific approach could be utilised for specific output desires. For example if larger clusters are required then an approach using a low nanoparticle to surface ratio (ME) may be optimum whereas if dispersity is the more critical parameter then a higher ratio (BE) approach may be more suitable. While the BE approach, as shown from the data of FIG. 15 indicates, that the polydispersity of the cluster size distribution is improved, the growth stops when the clusters are quite small (perhaps due to saturation of the surface or depletion of the suspension) and the process is slow. The advantage of ME is the speed of growth (but the dispersity is poor), at least over a standing suspension. Furthermore, one could utilise the differences in growth rates to use an initial ME approach to generate some clusters rapidly which are then fed through to another volume where they are used to seed particles which are being activated using a BE approach.

This phase was followed after 50-60 hours by a phase with very slow growth. There are breaks in the data in FIG. 13, run 2 where the PCS spectrometer was being used for other experiments. The cuvette was carefully removed and kept in a constant temperature bath at 25° C. during these periods. On restarting the experiment the position of the cuvette and laser attenuation were automatically adjusted, so there are discontinuities in the counts in FIG. 14.

The fact that the growth of the clusters still lies along the same straight line after the interruption is interesting, it demonstrates that moving the cuvette did not upset the experiment and that the laser light in the PCS experiment does not have any effect on the nanoparticle cluster growth.

Figure 14:
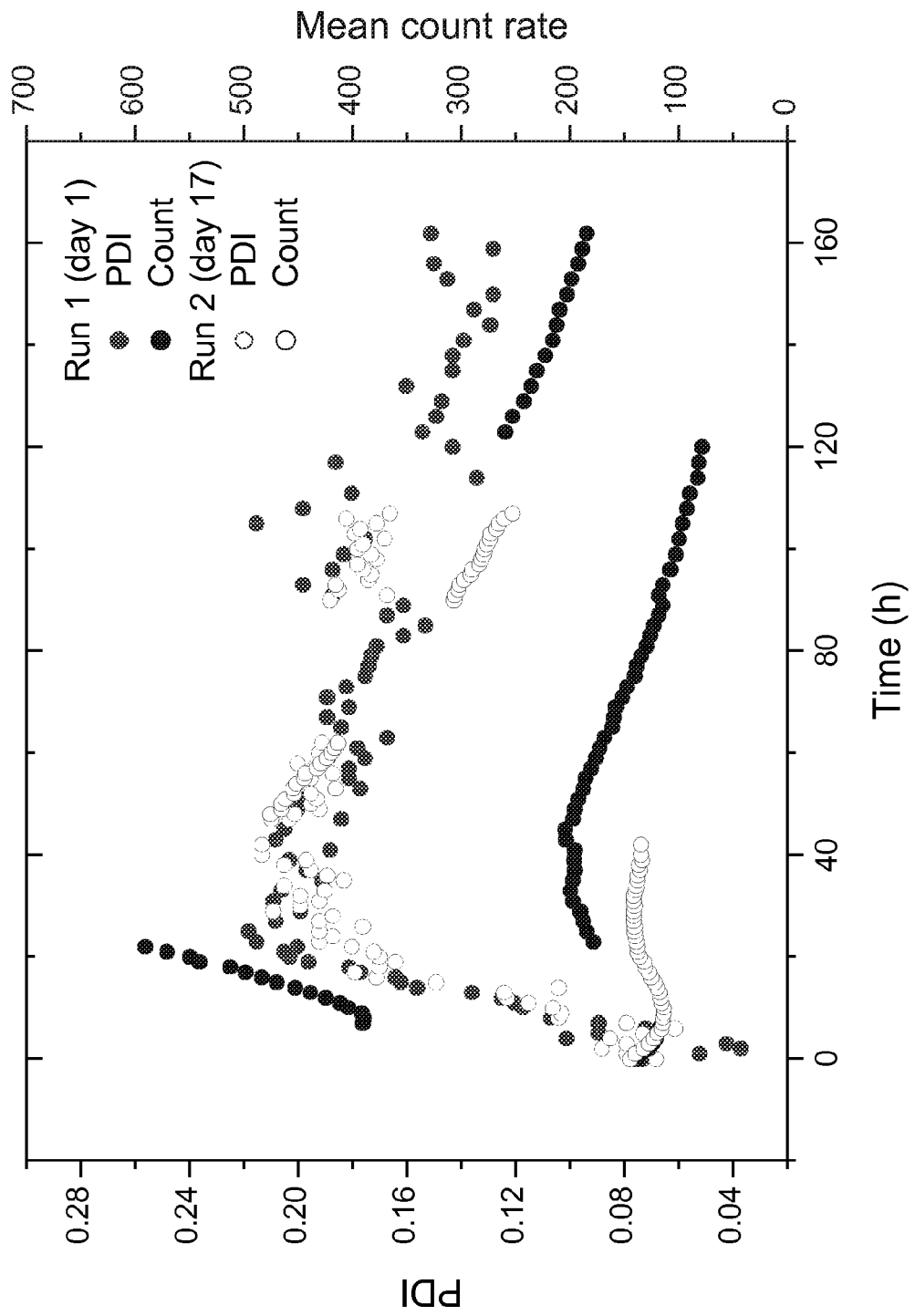

The change in PDI and count rate in the BE adsorption experiment in sample H5a are shown in FIG. 14. As was observed for the ME experiment (FIG. 7) the mean count rate increased continuously for the first 20-40 hours to about 500 kcps and then decreased for both runs.

Figure 15:
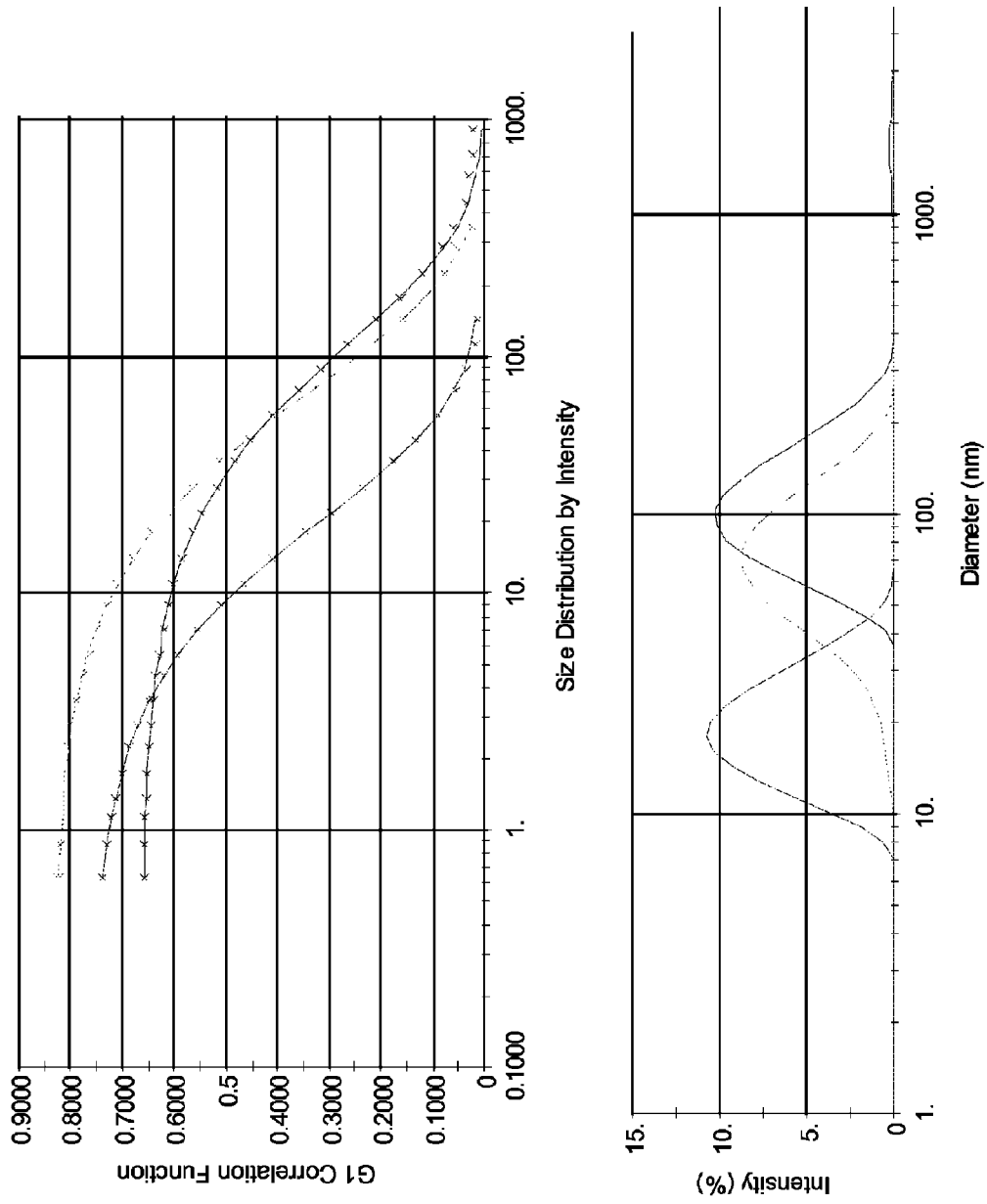
FIG. 15 shows PCS data fit and intensity size distribution for suspension H5a over porous silica-C18 substrate from the first run of the BE experiment, after 14 hours (—), 44 hours (—) and 120 hours (—).

The fit to the time correlation data and the resulting size intensity distributions for the BE experiment, with sample H5a, at three selected times is given in FIG. 15. The fits for the BE experiments are of better quality, with lower PDI values, than the ME experiments, in all cases the cumulants fit passes through the data. The cluster size distributions are not as broad during the BE experiments, again reinforcing the assessment outlined above that different approaches may be optimally selected for different objectives.

Figure 16:
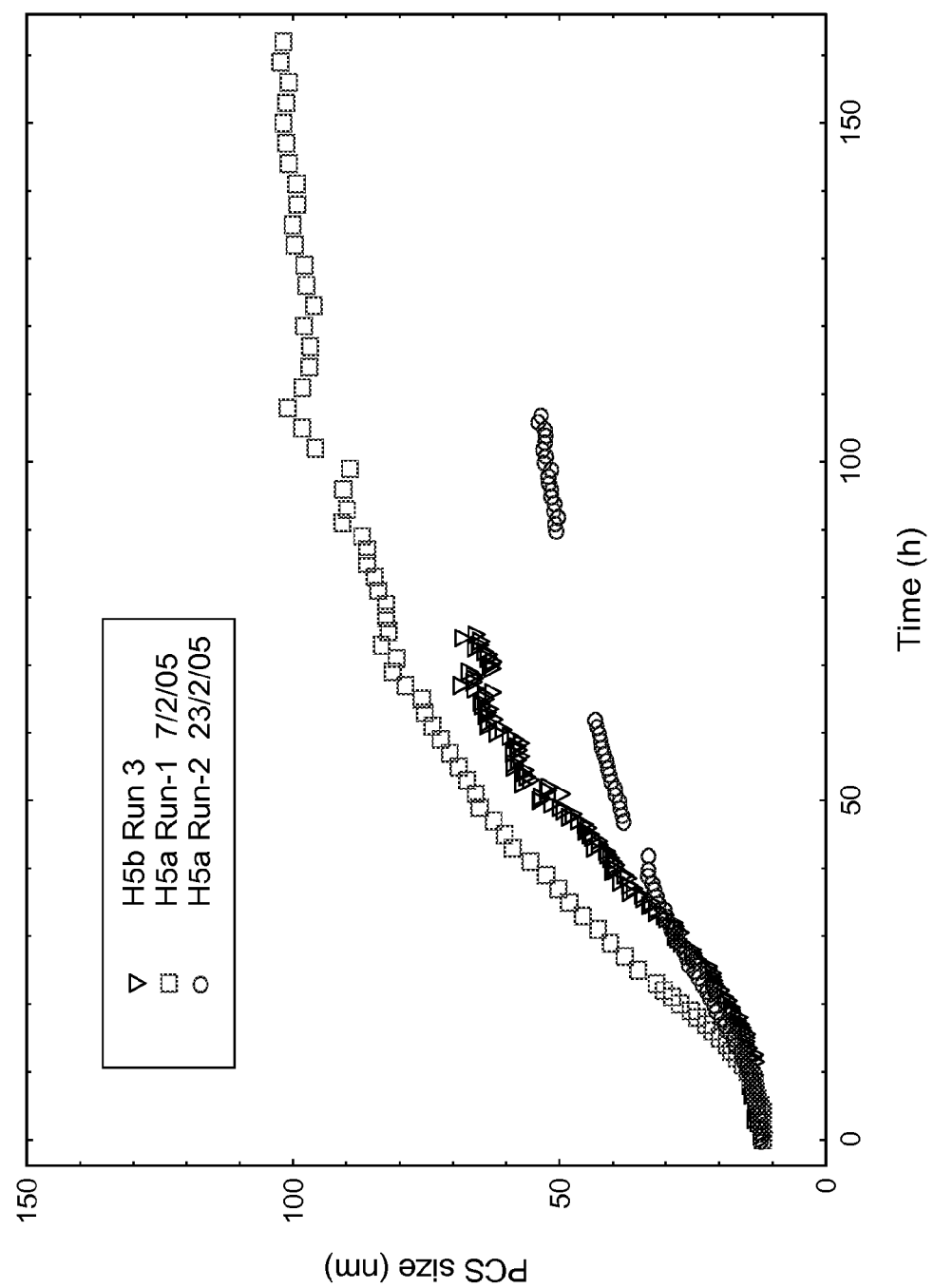
FIG. 16 shows Z-average data with time for three runs for an BE experiment (□) H5a run 1, (○) H5a run 2 and (∇) H5b run 3.

The data for the growth of the clusters from different preparations in the BE experiment is presented in FIG. 16. In general the hydrodynamic diameter (PCS size) increases up to about 50 h, after which there is some reduction in the growth rate. The trend of an increase in count rate time up to about 40 h, followed by a decrease was again observed. The counts were found to increase till about 40 hours in all the runs in BE addition.

Figure 17:
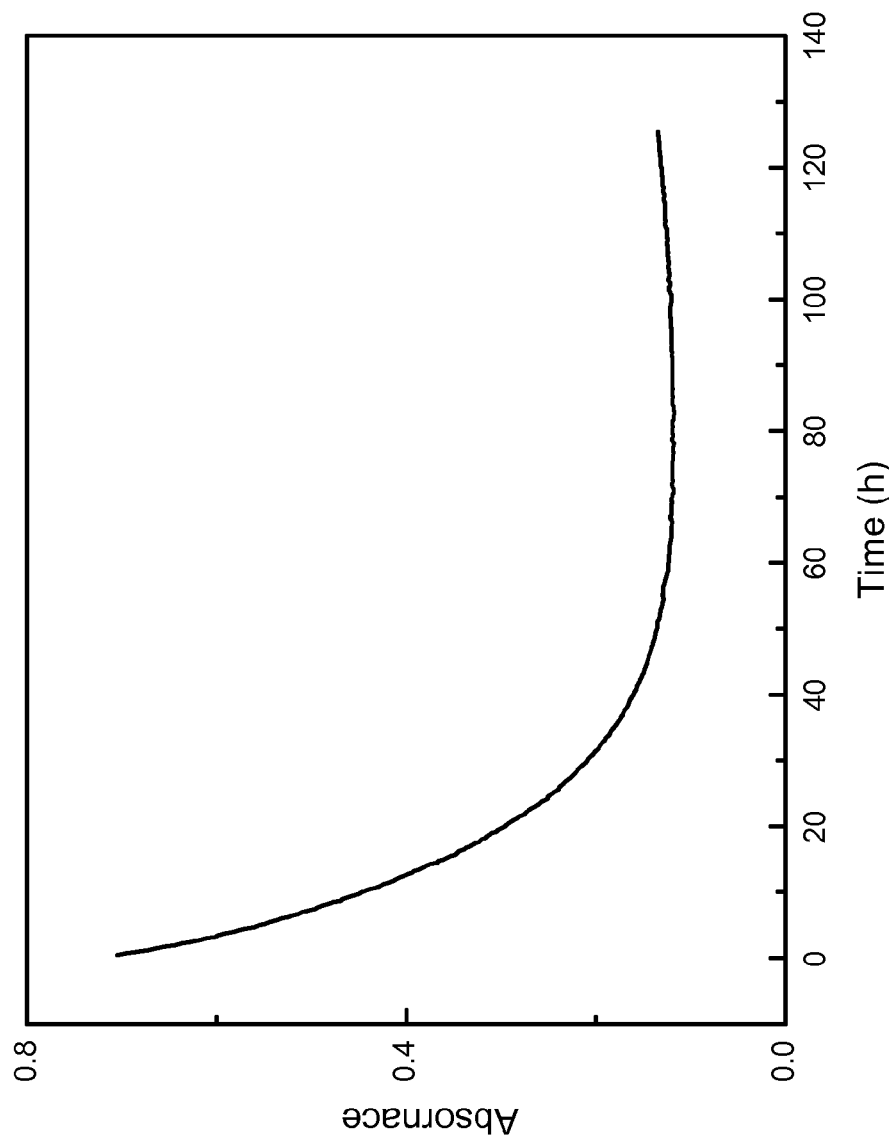
FIG. 17 shows UV absorbance at 475 nm over time for a BE experiment with H5b suspension over silica-C18.

The change in light absorbance of a BE magnetite suspension over silica-C18 was monitored over time, the data is presented in FIG. 17. As the experiment proceeded over 120 hours the absorbance decreased, in addition, the rate of decrease gradually diminishes. There are no discontinuities in the curve.

Further Experiments

An experiment was performed where a sample of oleic acid coated nanoparticles in heptane, was placed over untreated silica, instead of silica-C18. It was found that there is no clustering or adsorption in this case. This would appear to corroborate the assumption that the process requires an activation of the nanoparticles by an activator such as a substrate.

Figure 18:
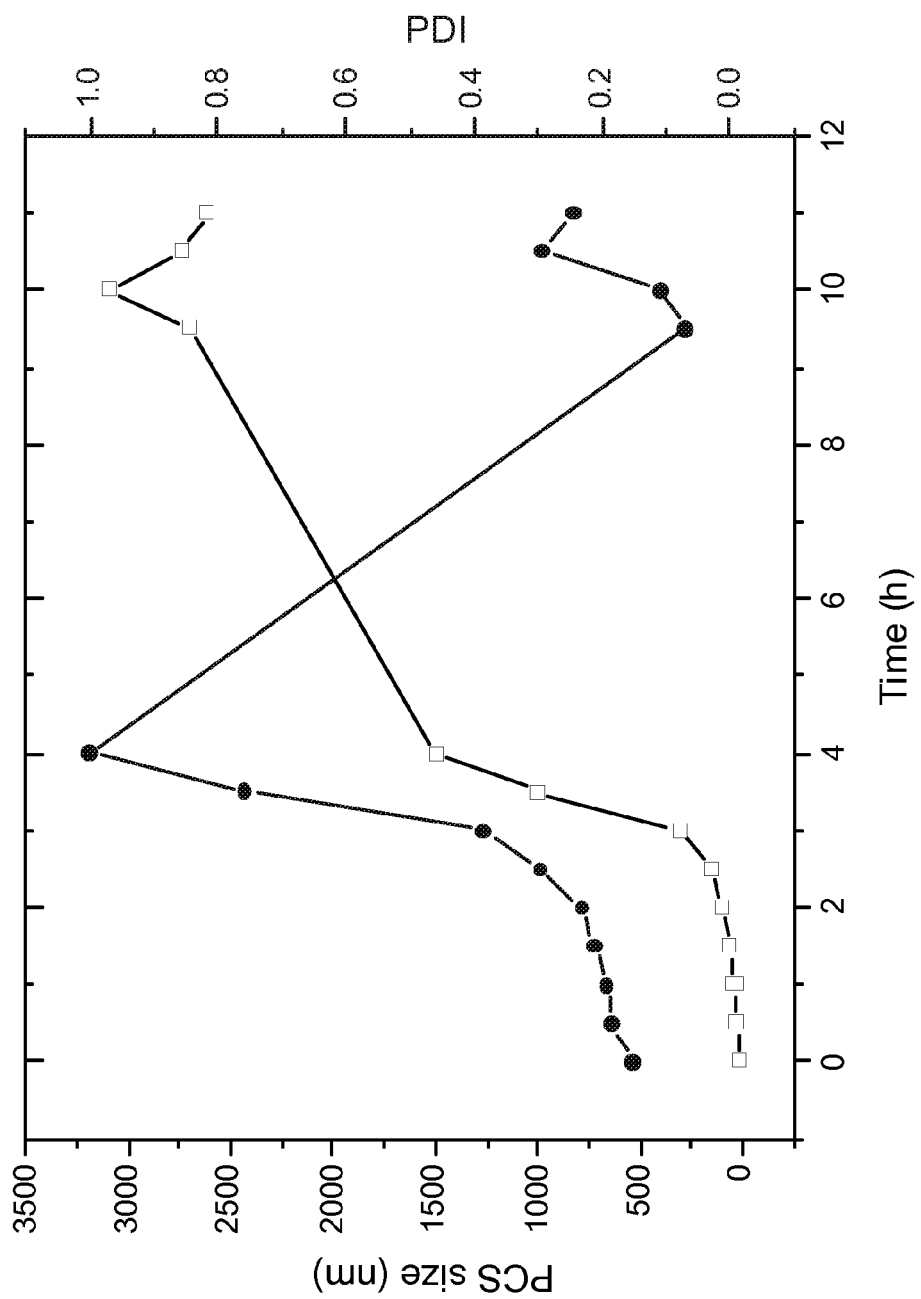
FIG. 18 shows PCS data for ME adsorption of magnetite suspension onto silica-CN substrate. The Z-average size is indicated with a (□), the PDI with (●).

An experiment was performed where a sample of oleic acid coated nanoparticles in heptane, was placed over anionic silica-CN, instead of silica-C18. It was found that there is rapid cluster growth into the μm range within 3 hours, see FIG. 18. The PCS software crashed after 4 hours, due to low scattering intensity. The later time points were run the next day after re-optimising the PCS spectrometer. In this way it will be understood that many active substrates would appear to suffice within the context of the process of the present invention. Indeed in the case of a silica CN substrate, subsequent experiments demonstrated that control could be exerted over the rate and extent of nanoparticle cluster formation.

A blank experiment was run using same quantity of silica-C18 substrate (50 mg) with pure heptane placed over it. PCS measurements were performed on the suspension after shaking it. The PCS data initially indicated particles of 82 μm size. This is due to the silica settling to the bottom of the cuvette. At no point over the following days were particles detectable. A cuvette was prepared containing 5 mM oleic acid in heptane over same quantity of silica-C18. This suspension also produced no suspended particles over two days, the PCS measurement crashed on each occasion. This would appear to corroborate the fact that the growth requires the nanoparticles to be in the suspension.

A series of adsorption experiments were performed where samples of oleic acid coated nanoparticles in heptane, were placed over silica-C18 and an aliquot of the solution removed at a given time, at which point the experiment was stopped. The iron content in the aliquots was then determined. After a period of days the suspensions are almost stripped of iron nanoparticles, which have been adsorbed onto the silica-C18. The physical appearances of the sample confirms this, the white silica-C18 substrate slowly becomes chocolate-brown coloured. In this it will be appreciated that the retrieval of clusters requires a removal of the cluster suspension before the clusters have precipitated out of solution onto the substrate.

Scanning Electron Microscopy (SEM)

Figure 19:
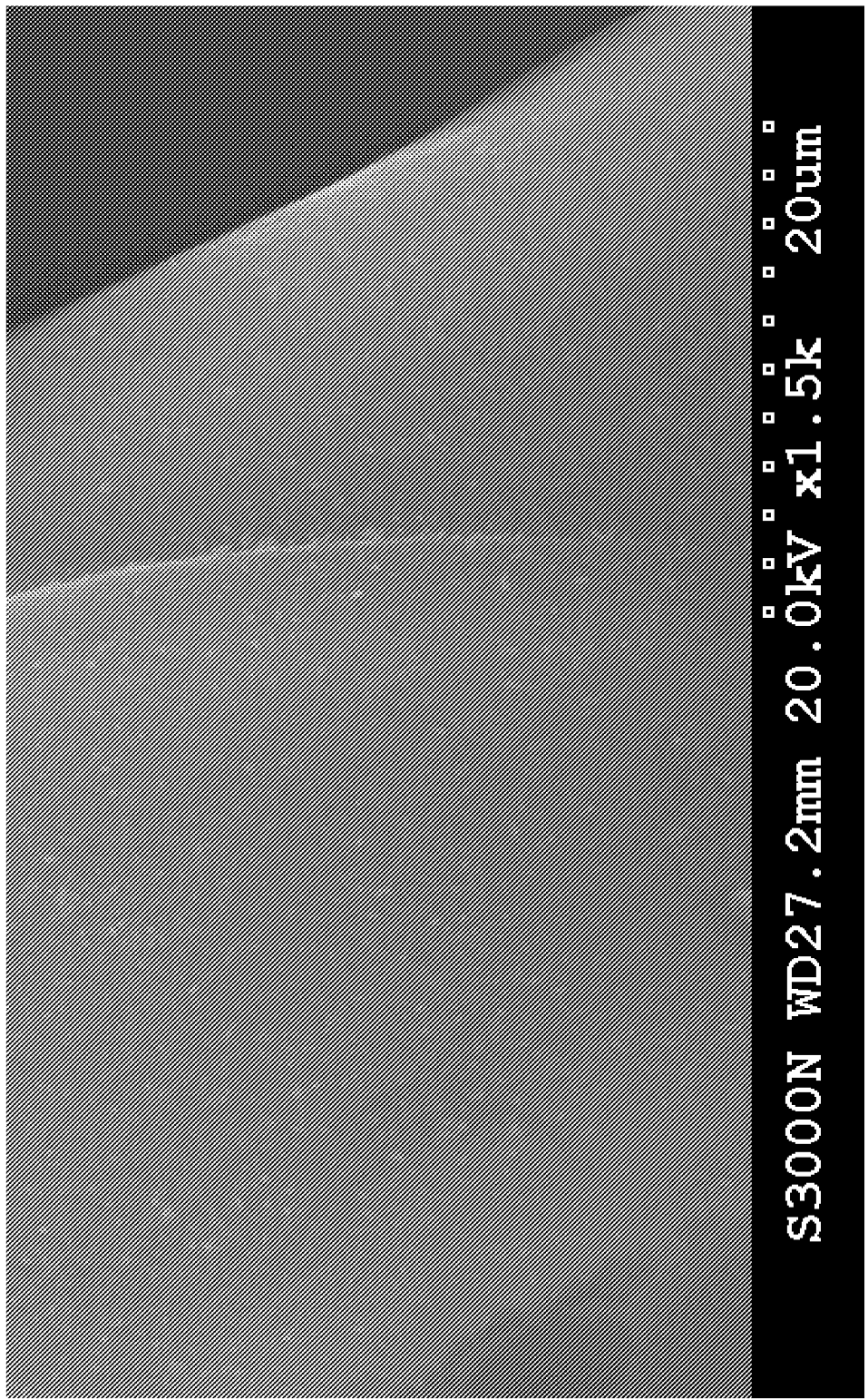
FIG. 19 is a scanning electron microscope image of fresh silica-C18 surface.

Samples for electron microscopy were prepared by spreading a drop of liquid on an SEM stub and allowing it to dry. The liquid was taken from the bottom of a cuvette, using a glass pipette, once the PCS measurement had ended. An 'uncoated' silica-C18 sample was prepared by splashing a pinch of powder on the tip of a spatula onto an aluminium SEM stub fixed with conducting carbon tape. SEM images of the silica-C18 particles under low magnification indicated that the particles in the range of 25-50 μm; with a few larger particles of up to 100 μm. The SEM image in FIG. 19 gives an insight of the fine morphology of the crystalline silica-C18 surface with very fine tiny white amorphous inclusions. Higher resolution images show the inclusions are in the size range from 50-200 nm. The micrographs of most of the regions of monolayer treated magnetite suspension indicated no coating of nanoparticles on the silica-C18 surface.

Figure 20:
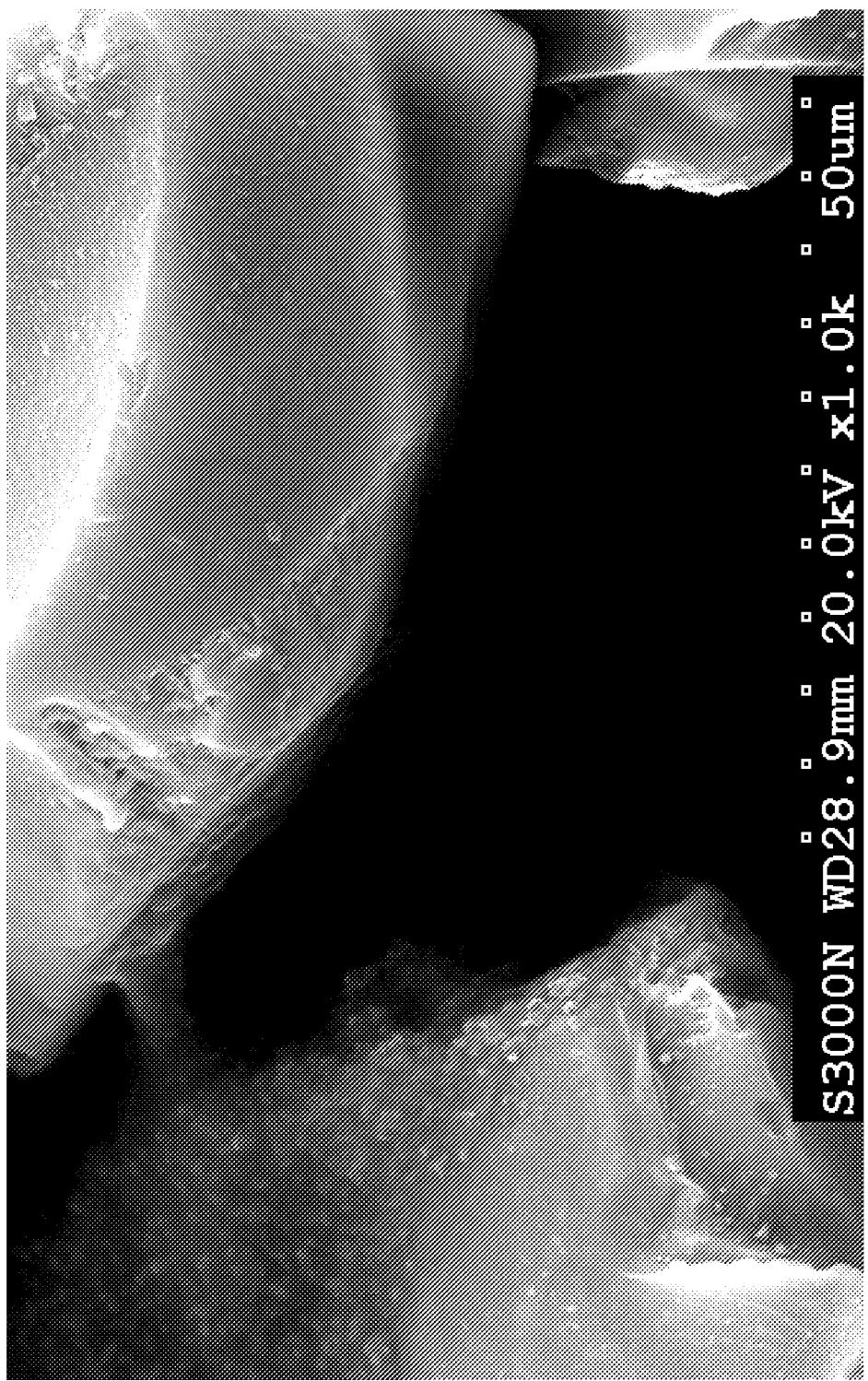
FIG. 20 is an electron micrograph of coated silica-C18 particles from a ME experiment.
Figure 21:
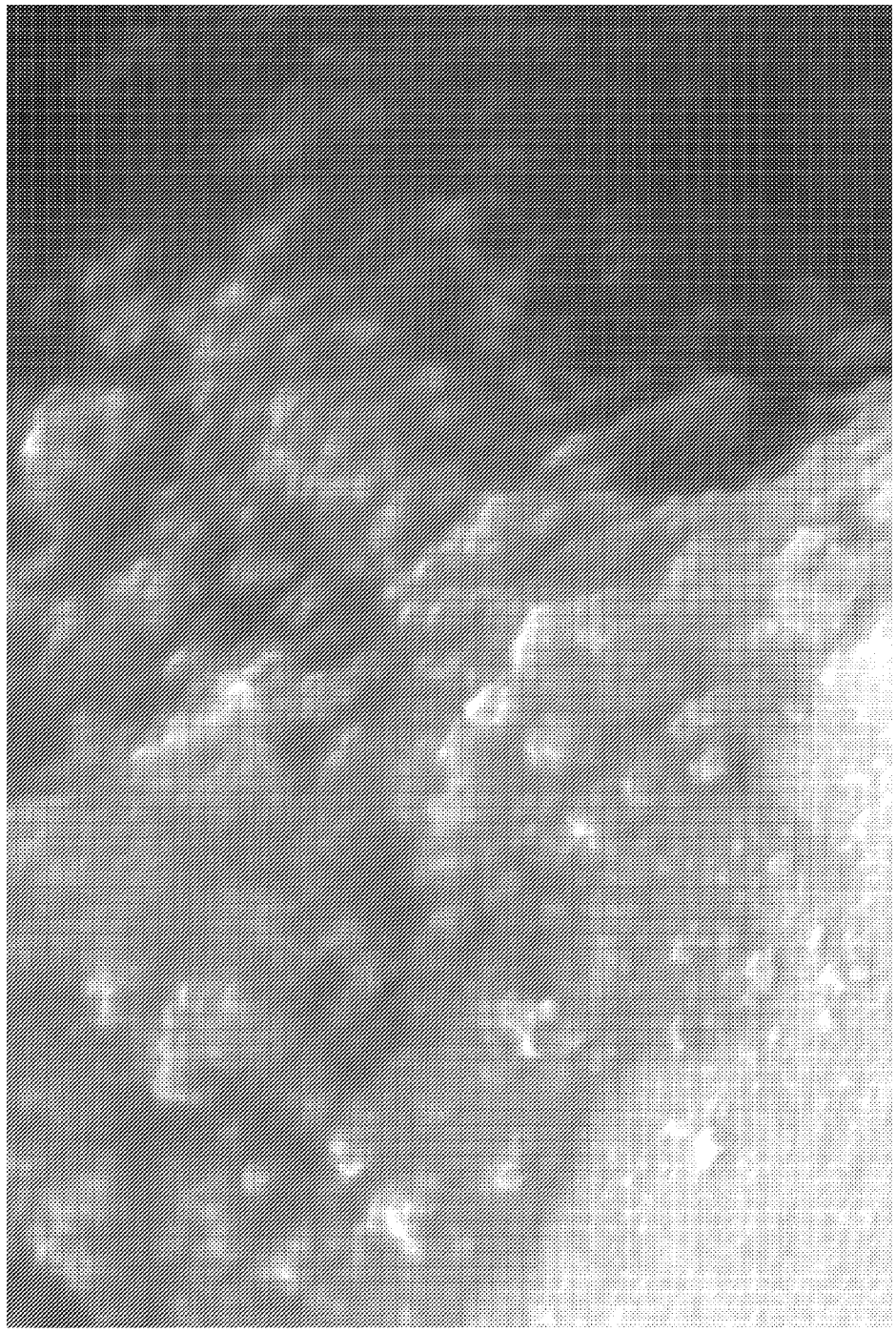
FIG. 21 is a magnified image of the region of FIG. 20 that was indicated by an arrow.

Magnetite nanoparticles were found to be deposited as large aggregates along edges, particularly in the vicinity of neighbouring silica particles. The arrow in FIG. 20 indicates one of such few regions of nanoparticle deposits, which was selected for the image shown in FIG. 21. The magnetic particle clusters are as big as 100-200 nm.

Figure 22:
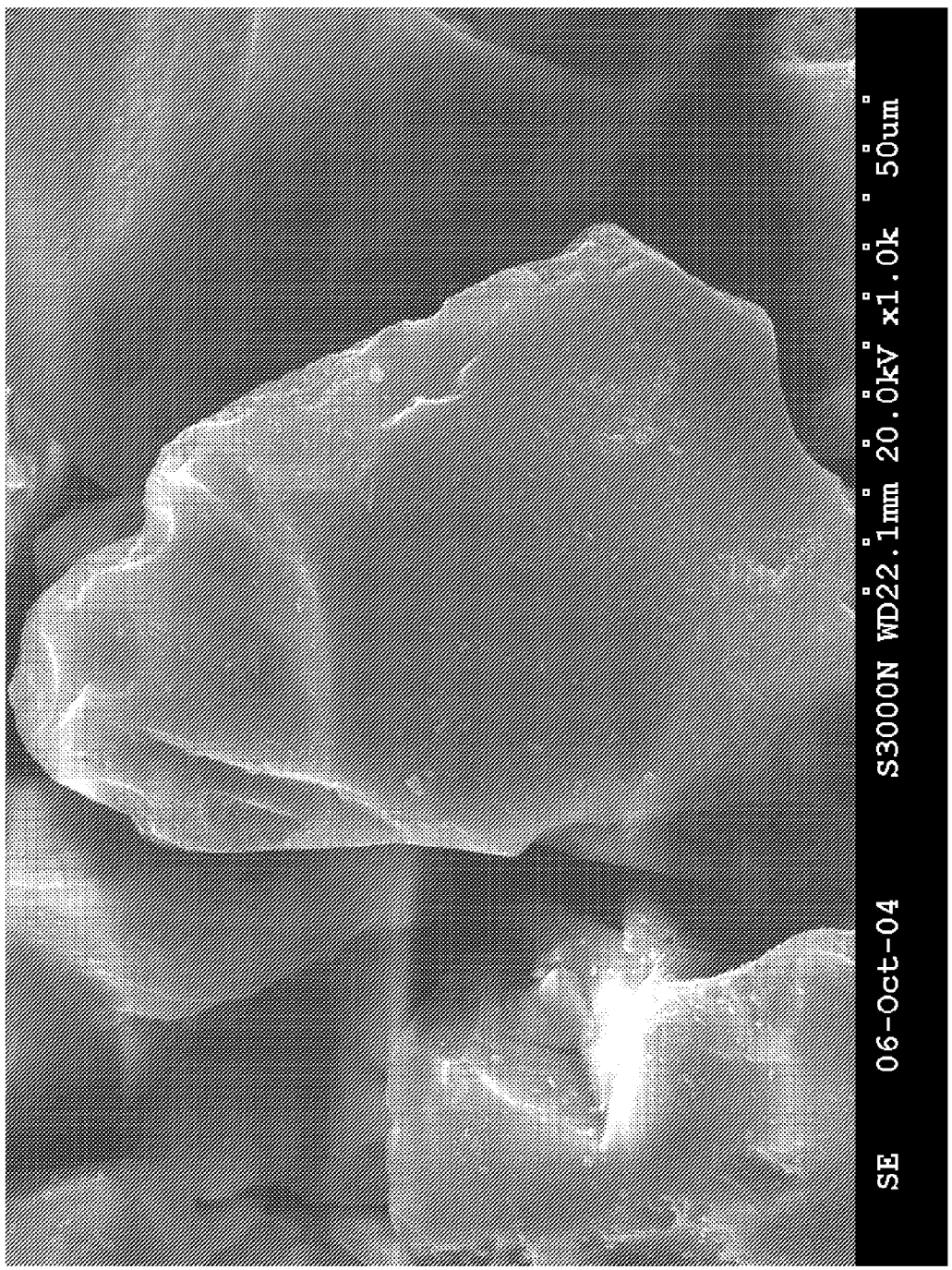
FIG. 22 is an electron micrograph of coated silica-C18 particles from a BE experiment.

There is no indication of any magnetite particle deposits on the flatter surfaces or in the junction between two particles, FIG. 22. Furthermore AFM studies did not provide any evidence of the presence of nanoparticles on the flatter surfaces. Thus the ME and BE designations refer in effect to high and low magnetite concentration samples. It will therefore be appreciated that within the context of the present invention that the terms ME and BE are intended to define high and low ratios of nanoparticles to their activating substrate, Discussion NMR and PCS measurements confirm that suspensions H5a and H5b are very stable even after couple of months from the date of synthesis. It was very clear by visual observation that the suspensions placed over silica-C18 were being depleted of iron oxide with time. The adsorption is confirmed by absorbance measurements and by iron determination.

For the ME adsorption experiments the Z-average cluster size increased slowly in a linear fashion for the first few hours. This was followed by a transitional phase of faster growth, up to around 12 hours. This phase was associated with an increase in the backscattered light intensity and an increase in the PDI to around 0.2. At this time the clusters are in the region of 100 nm diameter. There then followed a phase of very rapid linear growth (of the order of 100 nm/hour) that resulted in clusters in the μm range within a few hours. This phase was associated with a decrease in scattered light and an increase in the PDI up to the maximum value of 1.0. The data acquisition invariably stopped, due to low backscattered light intensity, within 24 hours.

For the BE adsorption experiments, the cluster growth was generally slower, and was usually observed to occur in three stages. It started with a brief phase of slow linear growth, similar to the ME experiments, this was followed by another phase of linear growth at a faster rate (c. 0.5 nm/hour) and ended with a phase of slower linear growth (c. 0.25 nm/hour) in most cases. There were some experiments where growth continued more rapidly and in an anomalous fashion. As in the ME experiment the backscattered intensity increased, until the transition to the slower growth phase at about 40-60 hours, after which it began to decrease again.

There are some common features to the ME and BE experiments, there is an induction phase during which there is little change in the particle size, after which the cluster growth accelerates significantly. The backscattered light intensity grows to a maximum in both cases before decreasing as the iron concentration decreases. There are also significant differences, for the BE experiments the growth is slower and the clusters that remain in suspension do not grow to be as large. The growing clusters are also far more monodisperse for the BE experiment. For the BE experiments if there is an induction phase, it is much shorter than for the ME experiments.

Both the ME and BE experiments utilise a methodology wherein oleate stabilised magnetic nanoparticles are attracted to the alkyl-grafted silica phase. It is believed that the adsorption process proceeds at a rate too slow to be diffusion limited.

It is believed that during the induction phase the nanoparticles diffuse close to the silica surface. The majority of the particles are repelled, but those that encounter an edge may exchange a proton, a hydroxyl group, or an oleate group with the surface and are held by coulombic attraction. The data presented above strongly suggests that some of these particles subsequently desorb. The monolayer coating of the desorbed nanoparticle is disrupted, some of the oleic acid coating is now bound to the silica-C18, resulting in activated nanoparticles in suspension. It is not possible to speculate as to how long the particle remains on the surface before desorbing, indeed they may be adsorbed for a short time, but it is highly unlikely that the nanoparticles desorb as a charged entity. This observation of an induction period is consistent with the direct mechanism illustrated previously with reference to FIG. 1 and in the case of an iron-oxide:oleate:silica-C18 system. However it will be understood that while this observation is consistent with the specific process parameters described herein that the invention should not be construed as being limited to this mechanism as one or more other or alternative mechanisms could be useful in other arrangements.

The nature of the adsorption sites on the silica surface remains unclear, it is apparent that a monolayer is not formed over the surface and that the nanoparticles build up in clusters along edges of the silica particles. The SEM images suggest that the edges tend to face neighbouring silica particles, but this may arise as the particles dry on the SEM stub. It might be anticipated that the presence of impurities, such as aluminium oxide, in the silica may be responsible for the surface activity. However, clusters are observed to grow over C18-grafted silica of higher quality (lower impurity content), while no cluster growth is observed for untreated silica, but very rapid adsorption is observed for silica-CN. It should also be pointed out that while 11 nm magnetite particles will diffuse easily through the gaps between the silica particles, it is unlikely that the larger clusters will be able to do so.

At the end of the induction phase the population of surface activated nanoparticles in suspension exceeds a critical value. The duration of the induction phase varies somewhat, which may be related to the low probability of establishing nanoparticle deposits on the silica surface. In the ME experiments there is then aggregation between surface activated nanoparticles resulting in the growth of clusters. As the magnetite content is relatively low, there remains silica surface capacity for generating more surface activated nanoparticles. There is subsequently a gradual transition to a later phase of very rapid cluster growth, FIG. 9, which probably arises due to the aggregation of clusters. At some time the growing clusters precipitate, as is shown in FIG. 1.

In the BE experiments the cluster growth is slower and more controlled. The magnetite content is relatively high, so there is less available silica surface capacity for generating surface activated nanoparticles, which therefore constitute a smaller fraction of the total suspended matter throughout. Cluster growth is due to the addition of individual nanoparticles to the growing clusters. There is a strong tendency for all the clusters in the population to grow together, which suggests that the clusters at the upper end of the distribution are somewhat less reactive. There is eventually a transition to a phase of slower cluster growth, FIG. 13, which may be due to the complete depletion of the original 11 nm particles from the suspension. In FIG. 15 the curve at 44 hours still contains some nanoparticles, this corresponds to the time at which the initial growth begins to slow.

Thus from the experiments, it is concluded that the transient adsorption of oleic acid coated magnetic nanoparticles from heptane suspension onto silica-C18 has been observed to occur while the remaining suspended particles continuously aggregate into clusters. The clusters can grow into the micron size range over a period of days. The rate of adsorption and cluster growth is orders of magnitude slower than is expected for a diffusion controlled process. This indicates that there is a significant energy barrier reducing the interaction of the nanoparticles with the silica surface, or that there is another process preceding adsorption. The observations are consistent with the dominant mechanism for nanoparticle cluster growth in this case being desorptive loss of temporarily adsorbed nanoparticles from the silica surface. This results in surface activated nanoparticles in suspension, for which the oleic acid coating has been partially removed. A small population of reactive nanoparticles are stabilised by interacting with other desorbed particles, mediating growth of clusters into the micron range, or until they bind irreversibly with the silica substrate.

Figure 23:
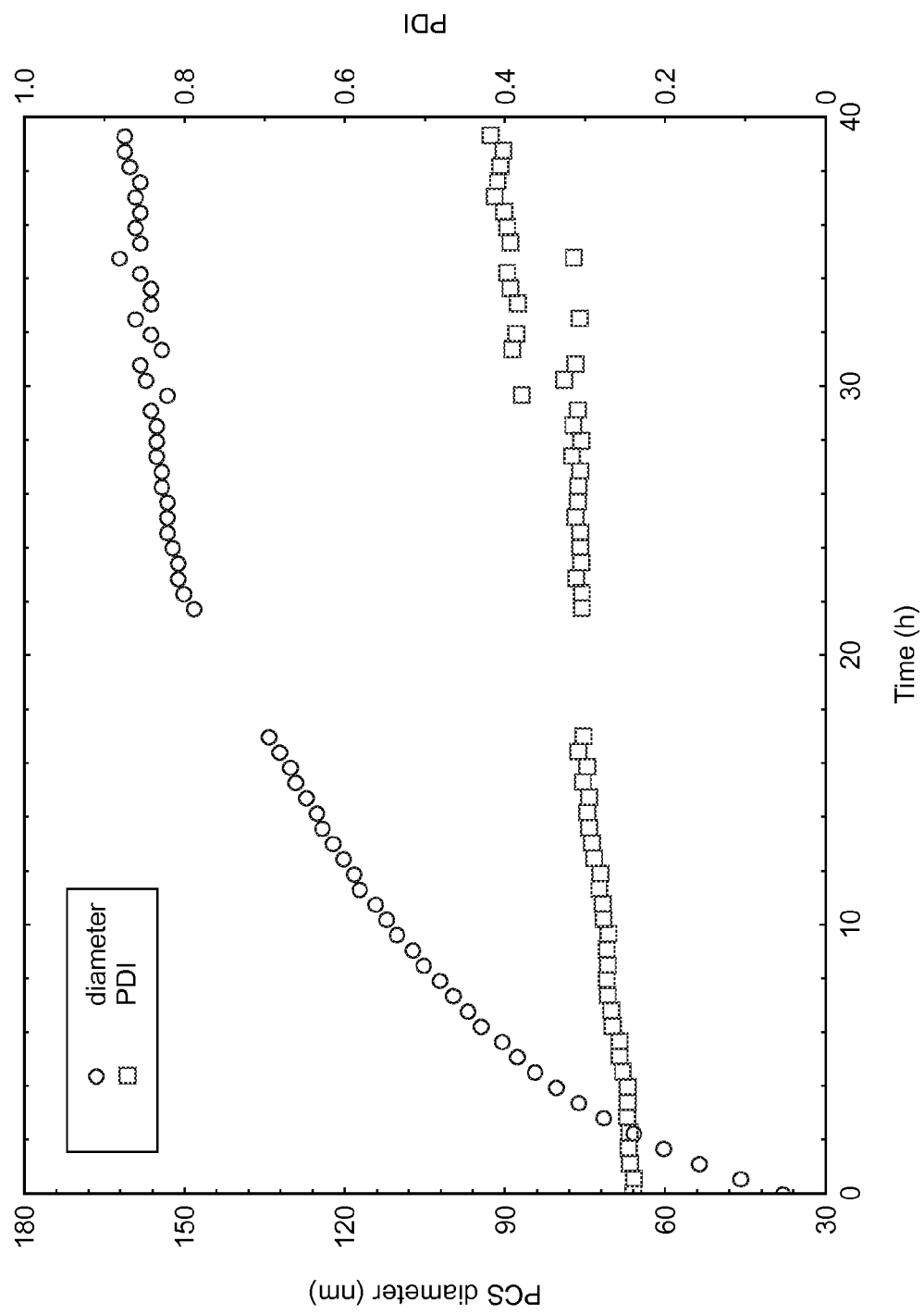
FIG. 23 shows PCS data fit and polydispersity index for a suspension of oleate coated nanoparticles prepared by a different synthetic route and placed over an alkyl grafted —C18 substrate from a different source to that of the results provided in FIG. 3.

Heretofore the invention has been described with reference to a nanoparticles generated using a technique advocated by Sun et al. The Sun approach produces coated nanoparticles. It will be understood that the invention is not to be construed as being limited to the formation of the initial stabilized nanoparticles using the Sun technique. For example, an experiment was performed where a sample of oleic acid coated nanoparticles, which were prepared by a different synthetic route, in heptane was placed over an alkyl grafted —C18 substrate obtained from a different source to that used in the previously described experiments. The nanoparticle preparation involved formation of a micro-emulsion and was based on a published procedure [Lee, H. S., Lee, W. C., Furubayashi, T. A comparison of co-precipitation with micro-emulsion methods in the preparation of magnetite, Journal of Applied Physics 1999, 85(8) 5231-5233.]. The substrate used was of higher quality than for the other experiments, possessing greater graft density and silica of greater purity. As shown in the PCS data of FIG. 23, it is evident that once again there was growth of nanoparticle clusters, to sizes in excess of 150 nm. This demonstrates that the process is not specific to particles prepared by the method of Sun or to a specific type, or source of, alkyl grafted silica. It will be noted that the breaks in the data presented in FIG. 23 correspond to times when the cuvette was removed from the PCS spectrometer. The instability in the extracted PDI at later times reflects poorer data quality associated with reduced particle concentration. This sample corresponds to many (>>10) monolayer equivalents.

It will be appreciated that heretofore the teaching of the invention has been described with reference to a specific example; that of the generation of magnetite nanoparticle clusters from a suspension of oleate coated iron oxide nanoparticles. This example has been provided to assist in an understanding of the general teaching of the present invention whereby by providing a substrate that exhibits an affinity for the capping agent on the nanoparticles—be that substrate for example be an alkyl modified silica or cyanted silica substrate—it is possible to effect a stripping the capping agent from the nanoparticle to create a reactive nanoparticle. Two or more reactive nanoparticles may interact with one another to effect generation of nanoparticle clusters. The general application of the teaching of the invention to any arrangement where a suspension including nanoparticles coated with a capping agent is brought into contact with a substrate that exhibits an affinity for the capping agent to generate reactive nanoparticles which combine to form nanoparticles is reinforced by another set of experimental data that follows.

Figure 24:
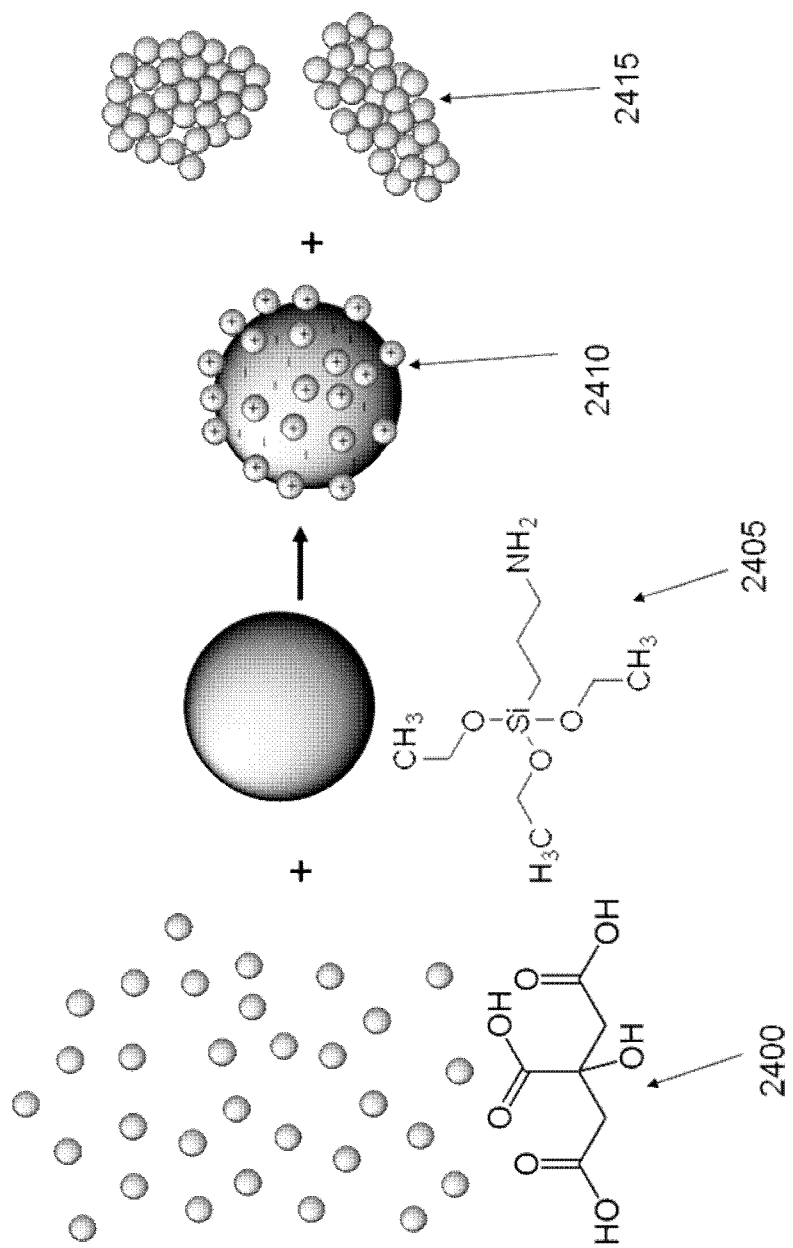
FIG. 24 shows a mechanism whereby citrate coated gold nanoparticles are stripped of their citrate capping agent through interaction with $NH_2$-modified silica particles to effect generation of gold nanoparticle clusters.

In this second arrangement, shown in FIG. 24, citrate coated gold particles are provided in a water solution (2400). The coated and stabilized nanoparticles are provided with a size distribution of about 16-17 nm. The suspension is brought into contact with a (3-aminopropyl) triethoxysilane-modified (APS-modified) silica substrate or particles of such a silica having dimensions of about 300 nm (2405). The affinity of the APS-modified silica to the citrate capping agent results in formation of a layer of nanoparticles on the surface of the substrate and the generation of reactive gold nanoparticles in the suspension (2410). Two or more of these reactive nanoparticles combine with one another to effect generation of gold nanoparticle clusters in a water suspension (2415). It will be appreciated that this reinforces the general application of the teaching of the invention as to how controlled growth of nanoparticle clusters can be effed through provision of capped nanoparticles and a suitable activating agent that exhibits an affinity for the capping agent.

Figure 25:
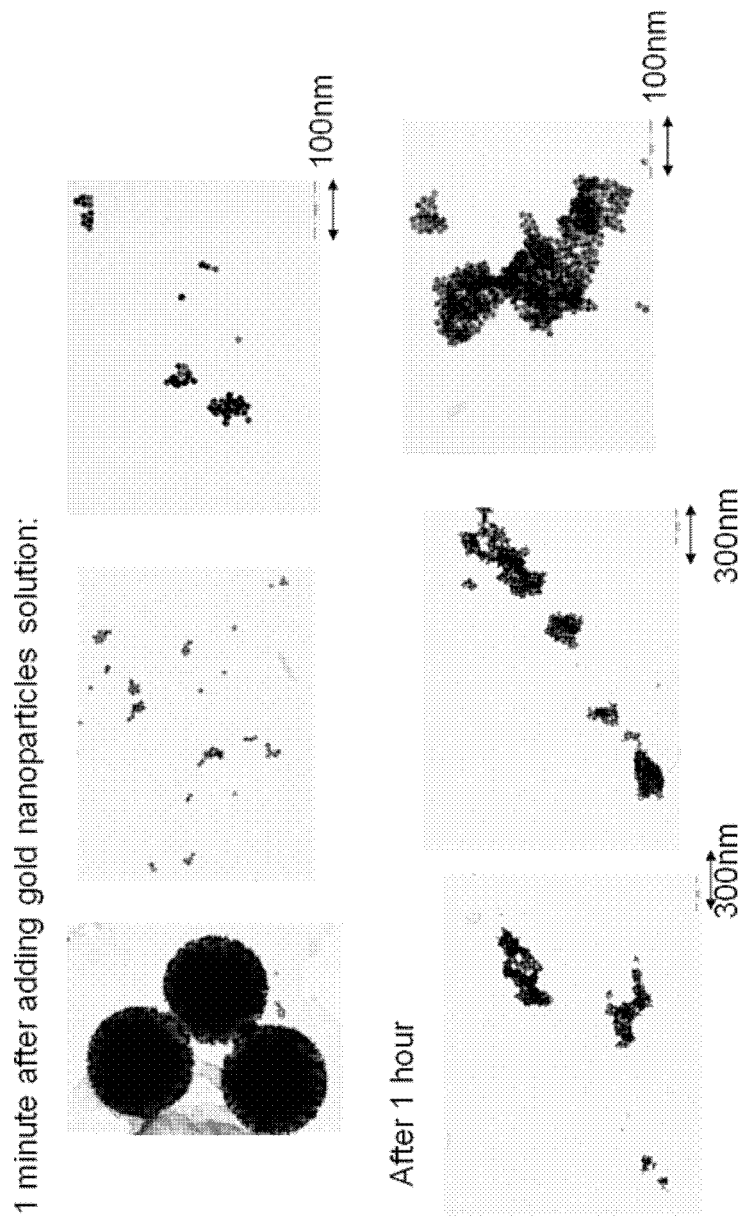
FIG. 25 shows examples of TEM images showing the growth of gold nanoparticle clusters.

FIG. 25 shows examples of TEM images of the gold nanoparticle nanocluster growth. It is evident that after a period of 1 hour that the size distribution of the clusters has grown to about 300 nm from less than the initial 100 nm after 1 minute exposure of the capped gold nanoparticles to the activating agent—in this case (3-aminopropyl) triethoxysilane (APS)-modified silica.

While the invention has been described with reference to preferred embodiments and compounds/materials it will be appreciated that such are described for exemplary purposes only and it is not intended to limit the invention in any way except as may be deemed necessary in the light of the appended claims. Thus for example, whilst the present invention has been described with reference to exemplary iron oxide and gold nanoparticles, it will be appreciated that it may also be advantageously employed with materials different to those described herein. What is important within the context of the teaching of the present invention is that an initially stabilized nanoparticle is activated through a stripping of the capping agent that provided the initial stabilization. This stripping is effected by providing an activating agent that exhibits an affinity for the capping agent and the stripping could be effected through either a direct, an indirect or a combination of the two mechanisms. Furthermore, the results or features described with reference to one figure or example could be interchanged with those of another figure or example without departing from the spirit or scope of the invention as it will be understood that an inter-changeability of integers or components may be possible and should be considered as falling within the teaching of the invention.

It will be understood that while exemplary methods of forming nanoparticle clusters have been described that the teaching of the present invention has application in the context of any process whereby initially stabilised nanoparticles are provided in a suspension and these stabilized nanoparticles are destablizised by effecting a stripping of the stabilizing capping agent from the surface of the nanoparticles. Two or more of these reactive or surface activated nanoparticles are then stabilised through interaction and combination with other reactive nanoparticles in the suspension, the stabilisation resulting in the formation of clusters of nanoparticles. Therefore while the invention has been described with reference to exemplary embodiments it is not intended that the invention be limited in any fashion except as may be deemed necessary in the light of the appended claims.

Furthermore the results presented in the experimental data are exemplary of the types of results that may be obtained using the teaching of the invention. Where they are explained with reference to certain underlying beliefs or understandings it is not intended that the invention be limited to such beliefs or understandings. The activation of a nanoparticle in suspension using an activation agent and the subsequent growth of clusters as is provided by the teaching of present invention should not be limited in any fashion except as may be deemed necessary in the light of the appended claims.

The words comprises/comprising when used in this specification are to specify the presence of stated features, integers, steps or components but does not preclude the presence or addition of one or more other features, integers, steps, components or groups thereof.

The invention claimed is:

1. A method of forming clusters of nanoparticles, the method comprising:
   a. providing a plurality of individually coated nanoparticles in suspension, the nanoparticles being coated with a plurality of surfactant molecules so as to be stabilized,
   b. subsequently bringing the suspension with the individually coated nanoparticles into contact with a material operable as an activating agent by its affinity to the surfactant molecules to provide for surface activation of individual nanoparticles by desorption of surfactant molecules from the surface of the coated nanoparticles to form two or more activated nanoparticles,
   c. allowing, through the expiration of time, the two or more of the activated nanoparticles to combine to form one or more clusters of nanoparticles in the suspension, in which each cluster includes a respective plurality of nanoparticles bound together, and d. subsequently removing the suspension from contact with the activating agent.

2. The method of claim 1, further including deciding when the formed clusters of nanoparticles are of a desired size and removing the suspension from contact with the activating agent when the desired size is obtained.

3. The method of claim 2 wherein the deciding is provided by monitoring the growth of the clusters of nanoparticles within the suspension.

4. The method of claim 3 wherein the monitoring is a continuous process.

5. The method of claim 3 wherein the monitoring is effected over a plurality of iterations.

6. The method of claim 2 wherein the deciding when the clusters of nanoparticles are of a desired size is effected after expiration of a predefined time period.

7. The method of claim 1 wherein the activating agent is a substrate.

8. The method of claim 7 wherein the substrate is a silica substrate.

9. The method of claim 8 wherein the silica substrate is formed from grafted silica.

10. The method of claim 7 wherein the concentration of the suspension to the activating substrate determines the growth of the clusters of nanoparticles.

11. The method of claim 7 wherein the concentration affects one or more of the rate and/or growth and/or size distribution of the clusters of nanoparticles within the suspension.

12. The method of claim 7 wherein the suspension is provided in a flow through arrangement, such that sequential volumes of suspension may be brought into contact with the substrate.

13. The method of claim 1 wherein the suspension includes magnetic nanoparticles.

14. The method of claim 1 wherein the suspension includes fatty-acid coated nanoparticles.

15. The method of claim 13 wherein the nanoparticles are iron-oxide nanoparticles.

16. The method of claim 1 wherein the nanoparticles are gold nanoparticles.

17. The method of claim 16 wherein the gold nanoparticles are coated with a citrate surfactant.

18. The method of claim 1 wherein the activating agent is a substrate and the surface activated nanoparticles are activated by adsorption of surface molecules from the nanoparticles onto the substrate.

19. The method of claim 1 wherein the activating agent is also in suspension.

20. The method of claim 18 wherein the activating agent in the suspension is an activated nanoparticle.

21. The method of claim 18 wherein the activating agent in the suspension is a cluster of nanoparticles.

22. The method of claim 18 wherein the activating agent is provided as a seeding agent to the suspension so as to provide for an acceleration or maintaining of the growth of the clusters of nanoparticles.

23. The method of claim 1 wherein the clusters of nanoparticles are formed from a desorptive loss of temporarily adsorbed nanoparticles from a substrate surface so as to form a surface activated nanoparticle in suspension, the surface activated nanoparticle being stabilized by interaction with other desorbed particles so as to mediate growth of clusters.

24. The method of claim 1 wherein the clusters of nanoparticles formed are selected from clusters in the range of 10 to 100 nm.

25. The method of claim 1 wherein the clusters of nanoparticles formed are selected from clusters in the range 100 to 1000 nm.

26. The method of claim 1 including stabilizing the clusters of nanoparticles.

27. The method of claim 26 wherein stabilizing the nanoparticle clusters provides for a cross-linking and phase transfer of the clusters of nanoparticles into a stable aqueous solution or an embedding of the clusters in a polymer matrix.

28. The method of claim 1 wherein the surfactant molecules provide a capping agent on the nanoparticles and the activating agent is selected on the basis of its affinity for the capping agent such that exposure of the capped nanoparticles to the activating agent effects a stripping of the capping agent from the nanoparticle to form a reactive nanoparticle.

29. A method of forming a drug delivery agent, the method including of:
   a. forming one or more clusters of nanoparticles in accordance with the method of claim 1, and
   b. encapsulating the one or more clusters of nanoparticles within a heat sensitive medium, the heat sensitive medium providing a carrier for a predefined pharmaceutical compositions.

30. A method of forming a catalyst, the catalyst having one or more clusters of nanoparticles formed on a surface of a substrate, the method including:
   a. providing one or more clusters of nanoparticles in accordance with the method of claim 1,
   b. applying the formed clusters of nanoparticles onto the surface of a substrate, and
   c. annealing the applied clusters of nanoparticles to provide for a thermal desorption of adsorbed species from the applied clusters of nanoparticles.

* * * * *